(12) United States Patent
Jagadeeswaran

(10) Patent No.: US 7,357,916 B2
(45) Date of Patent: Apr. 15, 2008

(54) METHOD FOR CREATING A UNIFORM VASCULAR WOUND IN ZEBRAFISH OR ZEBRAFISH LARVA

(76) Inventor: Pudur Jagadeeswaran, 3511 Elm Knoll, San Antonio, TX (US) 78230

( * ) Notice: Subject to any disclaimer, the term of this patent is extended or adjusted under 35 U.S.C. 154(b) by 224 days.

(21) Appl. No.: 10/525,571

(22) PCT Filed: Dec. 24, 2003

(86) PCT No.: PCT/US03/41249

§ 371 (c)(1),
(2), (4) Date: Jun. 30, 2005

(87) PCT Pub. No.: WO2004/092325

PCT Pub. Date: Oct. 28, 2004

(65) Prior Publication Data

US 2005/0244808 A1    Nov. 3, 2005

Related U.S. Application Data

(60) Provisional application No. 60/456,774, filed on Mar. 21, 2003, provisional application No. 60/436,270, filed on Dec. 24, 2002.

(51) Int. Cl.
*A61K 49/00* (2006.01)
(52) U.S. Cl. .................. 424/9.1; 424/9.2; 435/13; 436/69
(58) Field of Classification Search .............. 424/9.1, 424/9.2; 435/13; 436/69
See application file for complete search history.

(56) References Cited

U.S. PATENT DOCUMENTS 6,656,449 B1 * 12/2003 Serbedzija et al. .......... 424/9.2

OTHER PUBLICATIONS

Gregory M. et al. Genetic Analysis of Hemostasis and Thrombosis Using Vascular Occlusion. Blood Cells, Molecules and Diseases. 29(3)286-295, Nov./Dec. 2002.*
Jagadeeswaran P. et al. Methods in Cell Biology vol. 59, pp. 337-357, 1999.*
Jagadeeswaran et al. "Zebrafish: a genetic model for hemostasis and thrombosis." J Thromb Haemost 2004; DOI: 10.1111/ j. 1538-7836. 2004.00999.x.
Day et al. "Knockdown of prothrombin in zebrafish." Blood Cells, Molecules, and Diseases (In Press 2004).
Jagadeeswaran et al. "Developmental Expression of Thrombin in Zebrafish Embryos: A Novel Model to Study Hemostasis." Blood Cells, Molecules, and Diseases 23(9):147-156 (May 15, 1997).
Fisher et al. "Radiographic analysis of zebrafish skeletal defects." Believed to be publicly available at least as early as filing date of application, incomplete citation.
Thattliyath et al. "Young thrombocytes initiate the formation of arterial thrombus in zebrafish." Blood First Edition Paper, prepublished online Mar. 15, 2005; DOI 10.1182/blood-2004-10-4118.
Jagadeeswaran. "Zebrafish: a tool to study hemostasis and thrombosis." Curr Opin Hematol 12:149-152 (2005).
Andrade et al. "The use of the lipophilic fluorochrome CM-DiI for tracking the migration of lymphocytes." Journal of Immunological Methods 194:181-189 (1996).
Jagadeeswaran et al. "Effects of Hirudin (Thrombin Specific Inhibitor) in Zebrafish Embryos: A Developmental Role for Thrombin." Blood Cells, Molecules, and Diseases 23(21):410-414 (Nov. 15, 1997).
Abe et al. "Successful Treatment with Splenic Irradiation for Idiopathic Thrombocytopenic Purpura associated with Primary Immunodeficiency Syndrome." Jpn J Clin Hematol 40(11):1181-1186 (1999).
Andre et al. "CD40L stabilizes arterial thrombi by a B3 integrin-dependent mechanism." Nature Medicine 8(3):247-252 (Mar. 2002).
Balasubramanian et al. "Platelets, circulating tissue factor, and fibrin colocalize in ex vivo thrombi: real-time fluorescence, images of thrombus formation and propagation under defined flow conditions." Blood 100(8):2787-2792 (Oct. 15, 2002).
Bresch et al. "A Long-Term Toxicity Test Comprising Reproduction and Growth of Zebrafish with 4-Chloroaniline." Arch Environ Contam Toxicol 19:419-427 (1990).
Driever et al. "A genetic screen for mutations affecting embryogenesis in zebrafish." Development 123:37-46 (1996).
Gregory et al. "Selective Labeling of Zebrafish Thrombocytes: Quantitation of Thrombocyte Function and Detection during Development." Blood Cells, Molecules, and Diseases 28(3):418-427 (May/Jun. 2002).
Gregory et al. "Genetic Analysis of Hemostasis and Thrombosis Using Vascular Occlusion." Blood Cells, Molecules, and Diseases 29(3):286-295 (Nov./Dec. 2002).
Hanumanthaiah et al. "Developmental Expression of Vitamin K-Dependent Gamma-Carboxylase Activity in Zebrafish Embryos: Effect of Warfarin." Blood Cells, Molecules, and Diseases 27(6):992-999 (Nov./Dec. 2001).

(Continued)

*Primary Examiner*—Ralph Gitomer
(74) *Attorney, Agent, or Firm*—Gifford, Krass, Sprinkle, et al.

(57) ABSTRACT

Disclosed are improved methods for creating a uniform vascular wound in a zebrafish larva or zebrafish. The methods illustratively include subjecting a zebrafish larva to laser irradiation in an amount and for a period of time effective to cause a uniform vascular wound in the zebrafish larva; or exposing a zebrafish to water containing sodium hydroxide in an amount and for a period of time effective to cause a uniform vascular wound detectable in the gills of the zebrafish.

8 Claims, No Drawings

OTHER PUBLICATIONS

Hanumanthaiah et al. "Comprehensive Analysis of Blood Coagulation Pathways in Teleostei: Evolution of Coagulation Factor Genes and Identification of Zebrafish Factor VIIi." Blood Cells, Molecules, and Diseases 29(1):57-68 (Jul./Aug. 2002).

Hogan et al. "Mouse Models in Coagulation." Thromb Haemost 87:563-574 (2002).

Isogai et al. "The Vascular Anatomy of the Developing Zebrafish: An Atlas of Embryonic and Early Larval Development." Developmental Biology 230:278-301 (2001).

Jagadeeswaran et al. "A Hemophilia Model in Zebrafish: Analysis of Hemostasis." Blood Cells, Molecules, and Diseases 23(3):52-57 (Feb. 15, 1997).

Jagadeeswaran et al. "Analysis of Blood Coagulation in the Zebrafish." Blood Cells, Molecules, and Diseases 25(15):239-249 (Aug. 15, 1999).

Jagadeeswaran et al. "Identification and characterization of zebrafish thrombocytes." British Journal of Haematology 107:731-738 (1999).

Jagadeeswaran et al. "Analysis of Hemostasis in the Zebrafish." Methods in Cell Biology 59:337-357 (1999).

Jagadeeswaran et al. "Haemostatic screening and identification of zebrafish mutants with coagulation pathway defects: an approach to identifying novel haemostatic genes in man." British Journal of Haematology 110:946-956 (2000).

Jagadeeswaran et al. "Characterization of Zebrafish Full-Length Prothrombin cDNA and Linkage Group Mapping." Blood Cells, Molecules, and Diseases 26(5):479-489 (Oct. 2000).

Jain. "In Vivo Externalization of Phosphatidylserine and Phosphatidylethanolamine in the Membrane Bilayer and Hypercoagulability by the Lipid Peroxidation of Erythrocytes in Rats." J Clin Invest 76:281-286 (Jul. 1985).

Jalbert et al. "Inactivation of the Gene for Anticoagulant Protein C Causes Lethal Perinatal Consumptive Coagulopathy in Mice." J Clin Invest 102(8):1481-1488 (Oct. 1998).

Jayachandran et al. "Effects of ovariectomy on aggregation, secretion, and metalloproteinases in porcine platelets." AJP-Heart 284:1679-1685 (2003).

Joutsi-Korhonen et al. "Detection of reticulated platelets: estimating the degree of fluorescence of platelets stained with thiazole orange." Eur J Haematol 65:66-71 (2000).

Kurz et al. "Rat Model of Arterial Thrombosis Induced by Ferric Chloride." Thrombosis Research 60(4):269-280 (Nov. 15, 1990).

Lange et al. "Comparison of Testing Acute Toxicity on Embryo of Zebrafish, Brachydanio rerio and RTG-2 Cytotoxicity as Possible Alternatives to the Acute Fish Test." Chemosphere 30(11):2087-2102 (1995).

Michelmore et al. "Identification of markers linked to disease-resistance genes by bulked segregant analysis: A rapid method to detect markers in specific genomic regions by using sebregating populations." Proc Natl Acad Sci USA 88:9828-9832 (Nov. 1991).

Morrison et al. "Histological Study of the Development of the Embryo and Early Larva of Oreochromis niloticus (Pisces: Cichlidae)." J Morphol 248:172-195 (2001).

Nagel. "DarT: The Embryo Test with the Zebrafish Danio rerio—a General Model in Ecotoxicology and Toxicology." ALTEX: Alternativen zu Tierexperimenten 19(Supp 1):38-48 (2002).

Nasevicius et al. "Effective targeted gene 'knockdown' in zebrafish." Nature Genetics 26:216-220 (Oct. 2000).

Nechiporuk et al. "Assessment of Polymorphism in Zebrafish Mapping Strains." Genome Research 9:1231-1238 (1999).

Neilson et al. "Incorporation of a Subacute Test with Zebra Fish into a Hierarchical System for Evaluating the Effect of Toxicants in the Aquatic Environment." Ecotoxicology and Environmental Safety 20:82-97 (1990).

Postlethwait et al. "A Genetic Linkage Map for the Zebrafish." Science 264:699-703 (Apr. 29, 1994).

Qin et al. "Graft-versus-host reaction (GVHR) in clonal amago salmon, Oncorhynchus rhodurus." Veterinary Immunology and Immunopathy 89:83-89 (2002).

Reitsma. "Chapter 4—Genetic Principles Underlying Disorders of Procoagulant and Anticoagulant Proteins" Hemostasis and thrombosis: basic principles and clinical practice. Editors: Robert W. Colman et al. Philadelphia: Lippincott Williams & Wilkins (2001).

Rifkind et al. "Heinz Body Anemia—An Ultrastructural Study. I. Heinz Body Formation." Blood 25(6):885-896 (Jun. 1965).

Rinder et al. "Noninvasive Measurement of Platelet Kinetics in Normal and Hypertensive Pregnancies." Am J Obstet Gynecol 170:117-122 (1994).

Rinder et al. "Differences in Platelet alpha-granule Release between Normals and Immune Thrombocytopenic Patients and between Young and Old Platelets." Thromb Haemost 80:457-62 (1998).

Rinder et al. "Correlation of Thrombosis With Increased Platelet Turnover in Thrombocytosis." Blood 91(4):1288-1294 (Feb. 15, 1998).

Robetorye et al. "Update on Selected Inherited Venous Thrombotic Disorders." Am J Hematol 68:256-268 (2001).

Robinson et al. "Two colour analysis of reticulated platelets." Clin Lab Haem 22:211-213 (2000).

Robinson et al. "In vivo biotinylation studies: specificity of labelling of reticulated platelets by thiazole orange and mepacrine." British Journal of Haematology 108:859-864 (2000).

Rosen et al. "Laser-Induced Noninvasive Vascular Injury Models in Mice Generate Platelet- and Coagulation-Dependent Thrombi." Am J Pathol 158(5):1613-1622 (2001).

Saving et al. "Differences in Adhesion Receptor Expression Between Immature and Older Platelets and Red Blood Cells of Neonates and Adults." Journal of Pediatric Hematology/Oncology 24(2):120-124 (Feb. 2002).

Schafer. "Hypercoagulable states: molecular genetics to clinical practice." The Lancet 344:1739-1742 (1994).

Sheehan et al. "Demonstration of the extrinsic coagulation pathway in teleostei: Identification of zebrafish coagulation factor VII." PNAS 98(15):8768-8773 (Jul. 17, 2001).

Shimoda et al. "Zebrafish Genetic Map with 2000 Microsatellite Markers." Genomics 58:219-232 (1999).

Stohlawetz et al. "Effects of erythropoietin on platelet reactivity and thrombopoiesis in humans." Blood 95(9):2983-2989 (May 1, 2000).

Streisinger et al. "Production of clones of homozygous diploid zebra fish (Brachydanio rerio)." Nature 291(5813):293-296 (May 28, 1981).

Suttie. "The Biochemical Basis of Warfarin Therapy." Adv Exp Med Biol 214:3-16 (1987).

Tait et al. "Measurement of membrane phospholipid asymmetry in normal and sickle-cell erythrocytes by means of annexin V binding." J Lab Clin Med 123(5):741-748 (May 1994).

Takubo. "Reticulated Platelet and its Clinical Signifance." Rinsho Byora 50:761-767 (2002).

Williams et al. "Genetics of Arterial Prothrombotic Risk States." Exp Biol Med 226(5):409-419 (2001).

Wolf et al. "Erythropoietin Administration Increases Production and Reactivity of Platelets in Dogs." Thromb Haemost 78:1505-1509 (1997).

Yin et al. "Prothrombotic phenotype of protein Z deficiency." PNAS 97(12):6734-6738 (Jun. 6, 2000).

Zoller et al. "Thrombophilia as a multigenic disease." Haematologica 84:59-70 (1999).

Shannon Fisher et al., Radiographic Analysis of Zebrafish Skeletal Defects; Developmental Biology; 264; (2003) pp. 64-76.

* cited by examiner

METHOD FOR CREATING A UNIFORM VASCULAR WOUND IN ZEBRAFISH OR ZEBRAFISH LARVA

The present application is a United States nationalization of PCT International Patent Application PCT/US2003/041249, filed Dec. 24, 2003, which claims priority to first U.S. provisional application Ser. No. 60/436,270, filed Dec. 24, 2002, and to second U.S. provisional application Ser. No. 60/456,774, filed Mar. 21, 2003, the entire disclosures of which applications are specifically incorporated herein by reference without disclaimer.

The U.S. Government owns rights in the present invention pursuant to grant number HL63792 from the National Institutes of Health.

BACKGROUND OF THE INVENTION

1. Field of the Invention

The present invention relates generally to the field of thrombosis. The invention particularly provides zebrafish screening methods for use in identifying anti-thrombotic agents for therapeutic use and for use in identifying genes associated with all aspects of thrombus formation, including in humans. The preferred methods of the invention involve laser irradiation injury, sodium hydroxide-induced gill bleeding and red cell lysis assays conducted in zebrafish.

2. Description of Related Art

Thrombosis is a leading cause of death in the western world. According to Virchow, thrombosis arises from disturbances to three components: the vessel wall, the constituents of blood or the blood flow—classically known as Virchow's triad (Virchow, 1856). Recent studies on the components of Virchow's triad have shown that thrombosis is a multifactorial disease, involving the interaction of numerous factors leading to the formation of a thrombus, which may result in myocardial infarction, ischemia, and stroke (Zoller et al., 1999). In light of this multifactorial nature, it has been difficult to predict the occurrence of thrombotic attack.

Extensive genetic analysis of individuals with a family history of thrombosis has resulted in the identification of a limited number of genetic mutations and polymorphisms associated with an increased risk of thrombosis (Schafer, 1994). For example, genetic studies in humans identified factor V Leiden mutation and prothrombin 3'-end polymorphism as two of the more common mutations associated with increased risk of venous thrombosis (Reitsma, 2001). However, this analysis has not proven capable of identifying genetic risk factors in a significant number of the cases of inherited venous thrombosis (Reitsma, 2001; Robetorye & Rodgers, 2001). Even less is known about major genetic risk factors in arterial thrombosis (Williams & Bray, 2001). Additionally, the interaction between enviromnental factors and polymorphisms in hemostatic factors that lead to thrombus formation is poorly understood (Schafer, 1994).

A complete understanding of the various elements in Virchow's triad that contribute to thrombosis is clearly lacking. Further insight into additional genetic factors affecting thrombosis, as well as an increased knowledge of in vivo thrombus formation, is therefore of paramount importance in improving human health.

In patients that suffer from a thrombotic attack, anticoagulant therapy is necessary. Heparin is currently the clinical anticoagulant drug of choice, and is used universally for prophylaxis of postoperative thromboembolism, in patients with stroke, during various surgical situations, and in procedures involving extracorporeal blood circulation. Extracorporeal blood circulation is employed in numerous clinical situations, such as kidney dialysis, open-heart operations, cardiac catheterizations, blood oxygenation, plasmapheresis, organ transplantation, and the implantation of artificial organs.

Systemic heparinization, however, has been reported to result in a high incidence of bleeding complications, with major bleeding occurring in 8% to 33% of patients who receive various forms of heparin therapy. This is one line of evidence highlighting the need for new anti-thrombotic agents for therapeutic use. The development of new therapeutic agents first requires in vitro and in vivo screening methods of sufficient predictive value to permit pre-clinical testing. Reliable screening methods are lacking in the field of thrombosis.

Two of the strategies that can be employed to identify additional genetic factors in thrombosis are, first, more extensive screening of human populations prone to thrombosis using recently available genomic information; and second, global genetic screens for thrombosis in biochemical and animal models. Although more extensive genetic screening in disease-prone human populations is useful, these analyses cannot be applied to the development of new pharmaceutical products to treat diseases and disorders associated with aberrant thrombosis.

Biochemical, cellular and animal screening assays useful in research in other systems, such as those relying on yeast or drosophila, are evidently unsuitable to studies of thrombosis, which requires intact hemostatic pathways. The mouse has been a popular model in genetic studies of disease, due to the availability of knockout technology. Knockout models of certain hemostatic factors have been generated in the mouse (Hogan et al., 2002). However, only a limited number of hypercoagulable states were produced in these genetic studies, such as the disruption of protein C (Jalbert et al., 1988) and protein Z (Yin et al., 2000).

Genetic studies of thrombosis in the mouse model are limited by the labor intensity of generating knockouts. In addition, the generation of null alleles may result in embryonic lethality, which yields no relevant information on thrombosis. Although mutagenesis techniques could potentially overcome this latter problem, by generating point mutations that may cause hypo- and hyperactive alleles in addition to null alleles, large-scale mutagenesis screens for identifing novel genes affecting thrombosis are unfortunately lacking in the mouse model.

Accordingly, there remains in the art a need for improved screening assays related to the study of thrombosis, particularly those that can be applied to the identification of risk factors indicative of thrombosis and to the development of anti-thrombotic agents for use in treatment. The development of assays in an animal model in which the hemostatic pathways are similar to those of humans and yet which are amenable to large scale screening is particularly desirable.

SUMMARY OF THE INVENTION

The present invention solves the foregoing long-felt needs in the art by providing improved screening methods for use in identifing anti-thrombotic agents for veterinary and clinical use and for identifying genes associated with all aspects of thrombus formation in animals and humans. The preferred methods of the invention use zebrafish larvae and adult zebrafish in screening methods with predictive value for humans. The methods preferably include laser irradiation injury assays in zebrafish larvae, in vivo sodium hydroxide-induced gill bleeding assays in adult zebrafish and in vitro red cell lysis assays using blood from adult zebrafish.

The creation of uniform vascular wounds in zebrafish larva or zebrafish is an important aspect of the present invention. Accordingly, the invention provides methods for creating a uniform vascular wound in a zebrafish larva or zebrafish, which generally comprise:

(a) subjecting a zebrafish larva or a population of zebrafish larvae to laser irradiation in an amount and for a period of time effective to cause a uniform vascular wound in the zebrafish larva or larvae; and/or (b) exposing a zebrafish or a population of zebrafish to water containing sodium hydroxide in an amount and for a period of time effective to cause a uniform vascular wound detectable in the gills of the zebrafish or population thereof In terms of the larvae, the uniform wounding methods thus comprise subjecting a zebrafish larva, or a population thereof, to laser irradiation in an amount and for a period of time effective to cause a uniform vascular wound in the zebrafish larva or population thereof. In preferred embodiments, these methods comprise subjecting a zebrafish larva, or a population thereof, to laser irradiation in an amount and for a period of time effective to cause a reproducible thrombus in a major artery or a major vein of the zebrafish larvae or population thereof, wherein the reproducible thrombus is reversible so that circulation returns at the site of injury.

The zebrafish larva or larvae in such methods may be larva or larvae of three to five days postfertilization. The zebrafish larva or larvae may also be anesthetized, if desired, and/or immobilized in agarose for ease of use.

Laser irradiation is preferably applied to one or more major blood vessels of the zebrafish larva or larvae, thereby causing a uniform injury in the blood vessel or vessels. The laser irradiation may be applied to one or more major arteries, one or more major veins or a combination of one or more arteries and veins of the zebrafish larva or larvae.

As to the fish, the uniform wounding methods comprise exposing a zebrafish, or a population thereof, to water containing sodium hydroxide in an amount and for a period of time effective to cause a uniform vascular wound detectable in the gills of the zebrafish or population thereof. The zebrafish may be of any size, up to and including a full grown adult zebrafish or population thereof. Preferably, these methods comprise exposing an adult zebrafish, or a population thereof, to water containing sodium hydroxide in an amount and for a period of time effective to cause a reproducible visible hemorrhage in the gills of the zebrafish or population thereof The uniform wounding methods of the invention are ideally suited for use in screening assays. Accordingly, the invention further provides uniform wounding methods in which the coagulation is measured. "Coagulation" may be "measured" by any convenient method, including the degree, amount or longevity of coagulation and/or by the time taken to induce coagulation.

Accordingly, the invention further provides uniform wounding methods in zebrafish larva, or a population thereof, in which the time to occlusion in one or more injured blood vessels of the zebratish larva or population thereof is determined. The counterpart uniform wounding methods in zebrafish, including adults, or a population thereof, include those in which the bleeding time in the gills of the zebrafish or population thereof is determined.

In addition, the present invention further provides improved assays and screening methods performed on isolated blood samples. These are generally termed the "red cell lysis assays" of the invention, which are performed in vitro. Although suitable for use with zebrafish, these methods are generally applicable to other animals, including mammals, rodents, particularly mice, and humans.

The invention thus provides methods for analyzing the clotting time of a blood sample, which generally comprise collecting one or more blood sample(s) in the presence of an effective intermediate level of an anticoagulant and determining the time required for red cell lysis, preferably significant red cell lysis. Where the blood sample(s) is a human blood sample(s), the blood sample(s) is collected in a capillary tube with a "reduced heparin coating". As applied to zebrafish, the zebrafish blood sample is collected in a "heparinized capillary tube".

The in vitro methods for measuring coagulation activity in zebrafish blood sample(s) particularly comprise collecting one or more zebrafish blood samples, preferably from adult zebrafish, in one or more heparinized capillary tube(s) and determining the time required for lysis, preferably significant lysis, of red cells in the blood sample(s). More preferably, the methods comprise collecting one or more zebrafish blood sample(s) in one or more heparinized capillary tube(s), centrifiging the capillary tube(s) to separate red cells from plasma, and determining the time required for a red color, preferably a significant red color, to develop in the plasma. The "red color" in the plasma is indicative of "red cells lysis".

In certain preferred embodiments, the invention thus provides methods for measuring the clotting activity of a zebrafish blood sample, comprising collecting a zebrafish blood sample in a heparinized capillary tube, centrifuging the capillary tube to separate red cells from plasma, and determining the time required for significant red cell lysis by measuring the time for a significant red color to develop in the plasma following lysis of the red cells To provide the screening assays of the invention, the uniform wounding and measurement methods and/or the red cells lysis assays are further combined with the manipulation of the environment in which the zebrafish larva, zebrafish, or populations thereof, are maintained and/or by the manipulation of the zebrafish larva or zebrafish themselves, or populations thereof.

As such, the zebrafish larva, zebrafish, or populations thereof, may have been first contacted with a candidate substance. This permits the ability of the candidate substance to alter the vascular wound, and/or to alter red cell lysis, to be tested. Alternatively, the zebrafish larva, zebrafish, or populations thereof, may be a mutant or genetically engineered zebrafish larva or zebrafish, or population thereof, preferably one of a population of mutant zebrafish larvae or zebrafish produced by large-scale mutagenesis. These embodiments permit the effect of the mutation or genetic engineering on the vascular wound created in the zebrafish larva, zebrafish, or populations thereof, to be determined, and/or the effect on red cell lysis to be determined.

Important aspects of the invention are method for analyzing coagulation in zebrafish, comprising:

(a) subjecting a zebrafish larva to an amount of laser irradiation effective to cause a uniform vascular wound and measuring the time to coagulation in the wound;

(b) exposing a zebrafish to water containing an amount of sodium hydroxide effective to cause a uniform vascular wound in the gills of the zebrafish and measuring the time to coagulation in the wound; or (c) collecting a zebrafish blood sample in a heparinized capillary tube and measuring the time required for significant red cell lysis in the sample.

Preferably, the methods for analyzing coagulation in zebrafish comprise:

(a) subjecting a zebrafish larva to an amount of laser irradiation effective to cause a uniform vascular wound and measuring the time to coagulation in the wound; or (b) exposing a zebrafish to water containing an amount of sodium hydroxide effective to cause a uniform vascular wound in the gills of the zebrafish and measuring the time to coagulation in the wound.

Any of the in vivo or in vitro methods for analyzing coagulation may be further combined with the manipulation of the environment in which the zebrafish larva, zebrafish, or populations thereof, are maintained and/or by the manipulation of the zebrafish larva or zebrafish themselves, or populations thereof, thereby arriving at the screening methods of the invention.

Accordingly, coagulation may be analyzed in a zebrafish larva, zebrafish, or population thereof, exposed to a candidate substance, or in a blood sample therefrom, following which the ability of the candidate substance to alter coagulation can be determined. The time to occlusion in an injured blood vessel of a zebrafish larva may be determined, as may the bleeding time in the gills of a zebrafish, and/or the red cell lysis in an isolated blood sample.

Where coagulation is analyzed in a mutant or genetically engineered zebrafish larva, zebrafish, or population thereof, or in a blood sample therefrom, the effect of the mutation or genetic alteration can be determined. The invention is suitable for use in high throughput screening, such that one, more than one, and preferably a plurality or population of, mutant zebrafish larvae, zebrafish, or blood samples therefrom, can be analyzed, including those produced by large-scale mutagenesis, preferably large-scale chemical mutagenesis.

Particular mutations in a selected gene can also be analyzed in the zebrafish larvae, zebrafish or in blood samples therefrom. These studies are suitable for analyzing genetically engineered zebrafish larva or zebrafish comprising an antisense oligonucleotide, or derivative thereof, which specifically inhibits a selected zebrafish gene, or in a blood from such a larva or zebrafish. Thus, the invention is suitable for analyzing gene "knockouts". The invention is also applicable to analyzing "transgenic" zebrafish larva or zebrafish, or blood samples therefrom, wherein coagulation isianalyzed in a zebrafish larva, zebrafish or blood sample therefrom, which expresses a heterologous or exogenous gene (wild-type or mutant), i.e., a "transgene" introduced into the zebrafish genome by the hand of man.

Screening assays for candidate substances are important aspects of the invention. Such methods include those for identifying a candidate substance that alters thrombosis, which generally comprise contacting zebrafish larvae, zebrafish, or a population thereof, with a candidate substance and determining the ability of the candidate substance to change the coagulation time in zebrafish blood, wherein a candidate substance that changes the coagulation time is indicative of a candidate substance that alters thrombosis. In such methods, the "ability to change the coagulation time in zebrafish blood" is measured by:

(a) creating laser irradiation vascular wounds in zebrafish larvae and measuring the occlusion time in the wounds in the presence and absence of the candidate substance;

(b) creating sodium hydroxide-induced vascular gill wounds in zebrafish and measuring the coagulation time in the wounds in the presence and absence of the candidate substance; or (c) collecting zebrafish blood samples in heparinized capillary tubes and measuring the time required for significant red cell lysis in samples from zebrafish in the presence and absence of the candidate substance;

The invention thus provides particular screening methods for identifying candidate substance(s) that alter thrombosis. A first of these methods comprises creating a uniform vascular wound in a zebrafish larva using laser irradiation and testing a candidate substance for the ability to alter the occlusion time in the wound in comparison to the occlusion time in a wound in a zebrafish larva in the absence of the candidate substance.

A second such method comprises creating a uniform vascular wound detectable in the gills of a zebrafish by exposure to sodium hydroxide and testing a candidate substance for the ability to alter the coagulation time in the wound in comparison to the coagulation time in a wound in a zebrafish in the absence of the candidate substance.

The third of such methods comprises collecting in a heparinized capillary tube a blood sample from a zebrafish exposed to a candidate substance and determining the red cell lysis time in the blood sample in comparison to the red cell lysis time in a counterpart blood sample collected from a zebrafish in the absence of the candidate substance.

Any one or more of the foregoing methods may detect a candidate substance with the ability to increase the coagulation time, which is indicative of a candidate anticoagulant, or may detect a candidate substance with the ability to decrease the coagulation time, which is indicative of a candidate coagulant. After identification, any such candidate substance may be purified, and optionally, formulated as a composition or a pharmaceutical composition, and an effective amount administered to a cell population, tissue, animal or human in need thereof.

Further important embodiments of the present invention are methods for identifying a gene associated with coagulation. These methods generally comprise creating a mutant zebrafish larvae or zebrafish comprising at least a first mutation in at least a first gene and determining the effect of the mutation(s) on coagulation time in zebrafish blood, wherein identifing a mutation that changes the coagulation time is indicative of a gene associated with coagulation. The effect of the mutation on coagulation time in zebrafish blood is measured by:

(a) creating laser irradiation vascular wounds in zebrafish larvae and measuring the occlusion time in the wounds in the presence and absence of the mutation;

(b) creating sodium hydroxide-induced vascular gill wounds in zebrafish and measuring the coagulation time in the wounds in the presence and absence of the mutation; or (c) collecting zebrafish blood samples in heparinized lcapillary tubes and measuring the time required for significant red cell lysis in samples from zebrafish in the presence and absence of the mutation.

Due to the power of the screening methods of the present invention, the invention is particularly suitable for analyzing mutant zebrafish larvae or zebrafish from a population of mutant zebrafish larvae or zebrafish produced by large-scale mutagenesis, preferably large-scale chemical mutagenesis.

Still further aspects of the invention are therefore methods for identifying a gene associated with coagulation, which generally comprise mutagenizing a zebrafish population, preferably using large-scale mutagenesis and more preferably using large-scale chemical mutagenesis, to generate a plurality of mutant zebrafish larvae or zebrafish and selecting a mutant with an altered coagulation time, thereby identifying a gene associated with coagulation. A "mutant with an altered coagulation time" is selected by:

(a) creating laser irradiation vascular wounds in a plurality of zebrafish larvae, measuring the occlusion time in the wounds and identifying a mutant with an altered occlusion time;

(b) creating sodium hydroxide-induced vascular gill wounds in a plurality of zebrafish, measuring the coagulation time in the wounds and identifying a mutant with an altered coagulation time; or (c) collecting a plurality of zebrafish blood samples in heparinized capillary tubes, measuring the red cell lysis time in the samples and identifying a mutant with an altered red cell lysis time.

Whether analyzing a particular mutant or a population of mutants, these methods of the invention further comprise mapping a gene or genes so identified, preferably isolating a gene or genes so identified, more preferably, sequencing a gene or genes so identified, and most preferably, identifying the human homologue of a gene or genes so identified.

In further aspects, the invention provides a purified extract of lamb ears leaves, a composition and a pharmaceutical composition comprising a purified extract of lamb ears leaves, wherein the purified extract of lamb ears leaves comprises a substantially non-toxic anti-thrombotic compound of not greater than 10 kD that prolongs red cell lysis and alters thrombocyte adhesion.

The invention further provides methods of inhibiting coagulation and/or thrombosis, comprising administering to a cell population, tissue, animal or human in need thereof a biologically, therapeutically and/or pharmacologically effective amount, or an anti-thrombotic amount, of a purified extract of lamb ears leaves, or a composition or pharmaceutical composition comprising such a purified extract of lamb ears leaves. The purified extract of lamb ears leaves comprises a substantially non-toxic anti-thrombotic compound of not greater than 10 kD that prolongs red cell lysis and alters thrombocyte adhesion.

In other embodiments, the invention provides methods for selectively identifying immature thrombocytes or platelets. The methods generally comprise:

(a) contacting a population of zebrafish blood cells with an effective amount of DiI-$C_{18}$ and identifying cells labeled by DiI-$C_{18}$, thereby identifying immature zebrafish thrombocytes; or (b) contacting a population of mammalian, such as human or murine, blood cells with an effective amount of ethidium bromide and identifying cells labeled by ethidium bromide, thereby identifying immature mammalian platelets, such as immature human or murine platelets.

The methods may further comprise separating the immature zebrafish thrombocytes so identified away from the population of zebrafish blood cells as a whole, thereby providing a purified or substantially purified population of immature zebrafish thrombocytes. Equally, methods may further comprise separating the immature mammalian platelets, such as immature human or murine platelets, so identified away from the population of mammalian blood cells, thereby providing a purified or substantially purified population of immature mammalian platelets, such as immature human or murine platelets.

DESCRIPTION OF ILLUSTRATIVE EMBODIMENTS

A. Coagulation

Knowledge of the extrinsic pathway of coagulation is mainly due to the ability to assay, purify and characterize specific factors involved in coagulation functions. The accessibility and availability of mammalian plasma has facilitated biochemical characterization of human coagulation proteins, and the molecular cloning of soluble coagulation factor genes. The broad use of in vitro coagulation assays has lead to the characterization of bleeding disorders related to defects in these plasma proteins. Despite such knowledge, however, the initiation of coagulation in vivo remains incompletely understood.

The tissue factor-factor VIIa pathway (extrinsic pathway) is responsible for generating adequate amounts of thrombin to trigger propagation of the coagulation response. In vitro modeling has demonstrated that propagation of the coagulation response is a threshold mediated event, influenced by the relative levels of tissue factor, factor VIIa, and tissue factor pathway inhibitor (TFPI). Thus, known or unknown factors that regulate activity of the factor VIIa-tissue factor complex will determine the threshold for triggering of the coagulation response. Based on current knowledge, these known factors may include increased factor VII expression, increased activation of factor VII, increased tissue factor expression or activity, and decreased TFPI expression or activity.

A number of important questions remain regarding the generation of factor VII coagulant activity. A small fraction (<1%) of factor VII circulates in the two-chain active protease form under basal conditions, however, the in vivo mechanism for generating factor VIIa remains unclear. A variety of proteases can activate factor VII in vitro (including thrombin, factors XIIa, IXa, and Xa), and autoactivation of the zymogen factor VII bound to tissue factor has also been demonstrated. However, the reported rates of in vitro autoactivation vary significantly, occurring only slowly on cell surfaces, as compared to rates observed with relipidated tissue factor preparations. Thus, the in vivo mechanism for generating increased levels of factor VIIa remains unclear.

Increased levels of factor VII coagulant activity have been reported to be a risk factor for the development of ischemic heart disease. However, the measurement of factor VII coagulant activity is complicated by the potential influence of multiple factors, including total factor VII levels and relative levels of factor VIIa. Methods for directly measuring plasma factor VIIa have indicated that reduced levels are present in hemophilia B patients, which returned into the normal range following infusion of a highly purified factor IX preparation. These results suggest that factor IXa may be responsible for the basal levels of factor VIIa in vivo. However, elevated levels of factor VIIa have also been reported in a number of prothrombotic clinical states, including patients with acute coronary syndromes and the lupus anticoagulant. The factors responsible for increased levels of factor VIIa in these prothrombotic states are unknown.

Determinants of the in vivo expression levels of factor VII and TFPI are also largely unknown. Conserved regulatory elements have been described in homologous genes such as prothrombin, factors VII, and factor X, suggesting a common transcriptional mechanism for the coagulation proteases. Severe factor VII deficiencies have been associated with mutations in promoter binding sites for transcription factors such as hepatocyte nuclear factor-4 and Sp-1. While significant knowledge can be obtained by dissection of promoter regions in vitro, it is more difficult to definitively demonstrate these mechanisms are important in vivo.

Likewise, genes required for the post-translational vitamin K-dependent gamma-carboxylation of the coagulation proteases remain unidentified. The vitamin K-dependent carboxylase has been identified, however, the enzyme(s) responsible for the epoxide reductase activity that recycles vitamin K back to the hydroquinone form remain unknown. Regulation of TFPI expression and activity is even less well understood. Basic questions regarding the function of this inhibitor remain, including the role of the third Kunitz domain, and regulation of endothelial expression by inflammatory stimuli.

Although, bleeding disorders of unknown etiology due to plasmatic factors are rare in the human population, artificially created mutants in mice have provided bleeding symptoms that have not been found in the human population. For example, the vitamin K-dependent carboxylase gene knock out has generated bleeding mice (Zhu et al., 1998). The identification of regulatory proteins such as thrombin activatable fibrinolysis inhibitor (TAFI) and protein C receptor suggest that additional novel regulatory factors may exist.

B. Zebrafish

The zebrafish is a freshwater tropical fish. Outside the natural environment, fertilized eggs of zebrafish, Brachydanio rerio, have been used as an alternative to the acute fish test, to investigate the acute toxicity of chemicals during the first 48 hours of embryo development (Lange et al., 1995; Nagel, 2002). A long-term toxicity test comprising reproduction and growth of zebrafish over three generations has also been described (Bresch et al., 1990). It has been suggested that a subacute test with zebrafish should be incorporated into a hierarchical system for evaluating the effect of toxicants in the aquatic environment (Neilson et al., 1990).

In certain methods, teleosts (bony fish) in general, including zebrafish, have been proposed for use in screening assays to identify toxic agents and agents that induce or protect against cell death (U.S. Pat. No. 6,299,858, specifically incorporated herein by reference). A further example concerns screening to identify agents with angiogenic activity (published U.S. patent application 2002/20020025297, specifically incorporated herein by reference). These methods can be performed using high throughput screening, e.g., in multi well plates (U.S. Pat. No. 6,656,449, specifically incorporated herein by reference). Other methods concern introducing heterologous cells into fish that remain viable, permitting analyses on the heterologous cells, the fish or both (published U.S. patent application 2002/0061291, specifically incorporated herein by reference).

A transgenic zebrafish model for the study of lymphocyte and haemopoietic cell differentiation, control and screening of therapeutic agents has also been described. This concerns transgenic zebrafish expressing a heterologous Ikaros protein (published U.S. patent application 2003/0028909, specifically incorporated herein by reference).

Transgenic zebrafish models for neurodegenerative disorders have also been reported, which allow screening of compounds for their ability to protect and/or regenerate neurons in vivo (published U.S. patent application 2002/0187921). These transgenic zebrafish comprise a reporter gene that is under the control of a neuron-specific promoter, such that the product of the reporter gene is expressed in zebrafish neurons. This model may be used in identifying gene targets for neuroprotective compounds as well as identifying compounds that regenerate neurons and compounds that promote neurogenesis (published U.S. patent application 2002/0187921, specifically incorporated herein by reference). Indeed, cell lineage-specific expression in transgenic zebrafish is now possible, meaning that transgenic fish can be generated to stably express heterologous genes ("transgenes") in tissue- and/or developmentally-specific patterns (U.S. Pat. No. 6,380,458, specifically incorporated herein by reference).

Zebrafish have also been described for use in screening methods using ribozymes (U.S. Pat. No. 6,355,415). In such methods, a zebrafish genomic sequence that encodes a cleavable RNA and has homology to a human sequence is contacted with a ribozyme. Following ribozyme cleavage of the sequence, the resultant zebrafish cells, tissues or animals are monitored for particular morphological and/or behavioral changes, which permit function(s) to be assigned to the original target sequences (U.S. Pat. No. 6,355,415, specifically incorporated herein by reference).

The foregoing patents and patent applications evidence the ability to maintain and reproduce teleost and zebrafish embryos, larvae and adults and utilize them in screening assays, and are specifically incorporated herein by reference for such purposes. Various of the patent documents, such as 2003/0028909, 2002/0187921, 6,380,458 and 6,355,415, further demonstrate the high level of technical ability in the art concerning genetic manipulation in zebrafish, including recombinant expression, mutagenesis, mapping and gene cloning, and are further specifically incorporated herein by reference for such purposes. However, none of the foregoing patents and patent applications concern coagulation.

Zebrafish provide a unique and important vertebrate model to study developmental and biochemical pathways. Zebrafish are amenable to large scale mutagenesis, demonstrate short generation times, have high fecundity, have the ability to rapidly generate homozygotes and are bred easily. Chemical mutagenesis with N-ethyl-N-nitrosourea (ENU) induces mutations at an average specific locus rate of approximately one in 500 zebrafish genomes, demonstrating that saturation of the genome is feasible (Driever et al., 1996). Mutagenesis of the zebrafish genome has yielded important insights into genes involved in cardiac, vascular and erythrocyte development, including models of disease such as sideroblastic anemia.

The zebrafish thus provides a vertebrate model amenable to a saturation mutagenesis approach. This approach allows the identification of genes in an "unbiased" manner, as opposed to the gene by gene approach employed by homologous recombination studies in the mouse. Saturation mutagenesis can identify genes that contribute significantly to a given pathway, which can result in identification of novel factors or new functions for known genes. The ability to identify novel genes on the basis of in vivo function provides a significant advantage, and subsequent identification of human homologues is then possible.

Several lines of evidence suggest that hemostatic system in fish is similar to that of mammals, i. e., fibrin deposition and platelet aggregation. Homologous cDNAs for prothrombin and fibrinogen have been isolated from a number of fish species. Although fish are a diverse collection of species, cDNAs for prothrombin have been demonstrated in both primitive species such as the hagfish (Class Myxini) and the modern bony fish (Class Osteichthyes). Bony fish (teleosts) demonstrate factor X like activity, response to thromboplastin, protein C activity and an anticoagulant response to warfarin. A consumptive coagulopathy representing diffuse intravascular coagulation also occurs in salmonid fish (salmon and trout) with bacterial flirunculosis. Likewise, the nucleated thrombocyte in fish appears to be the equivalent of the mammalian platelet, demonstrating surface attachment and spreading, a surface-connected canalicular system, and aggregatory responses that require the presence of fibrinogen. Additionally, catfish (*Ictalurus punctatus*) demonstrate thrombocyte specific expression of a GPIIb/IIIa-like complex, suggesting conservation of this integrin in bony fish.

The major hemostatic pathways in zebrafish are similar to those existing in mammals (Jagadeeswaran et al., 1999b). Several cDNAs for zebrafish coagulation factors have been cloned, sequenced and shown to have a high degree of identity (40-45%) to the human homologues. These include cDNAs for zebrafish prothrombin (factor II), factor VII, a factor that is homologous to factor VII but has protein z characteristics, heparin cofactor II, antithrombin, factor V like molecule and plasminogen precursor like sequences. The predicted protein sequence for factor VII, for example, has 41% identity at the amino acid level to human coagulation factor VII and complete conservation of important structural features. The high degree of identity to the human homologues exists not only at the primary structure level, but also at the three dimensional structure level, e.g., as illustrated by homology modeling for factor VII.

Zebrafish plasma can cleave exogenous human fibrinogen to form human fibrin. Both factor X and protein C-like activity have been detected in zebrafish plasma. These studies showed that vitamin K-dependent γ-carboxylation is important for the function of zebrafish hemostatic protein(s). The presence of natural anticoagulant activities, including antithrombin-like inhibitors and heparin cofactor II, has also been demonstrated in zebrafish plasma using both clotting and chromogenic assays.

Studies have shown the presence of an intrinsic pathway of coagulation in the zebrafish. Several assays have indicated the presence of factor X-like activity in zebrafish, similar to the common pathway of coagulation in humans. An important finding is that the extrinsic pathway of coagulation in zebrafish is very similar to the human extrinsic pathway. This makes the zebrafish a suitable and unique model to study the defects in this pathway, which are relevant to mammals and humans, and to study complex disease such as thrombosis.

Zebrafish thrombocytes have also been identified by histological, morphological and electron microscope studies and shown to function similarly to mammalian platelets. Immnunofluorescence studies have shown that zebrafish thrombocytes have glycoprotein Ib (GPIb) and glycoprotein IIb/IIIa (GPIIb/IIIa)-like molecules on their surface, suggesting that the pathways for platelet adhesion and aggregation are conserved in the thrombocyte, which was confirmed by various functional studies. Functional assays further showed that intact agonist-stimulated secretory and cyclo-oxygenase pathways exist in the zebrafish thrombocyte, which could be inhibited by adding acetylsalicylic acid (ASA) to the water. These studies further demonstrate the feasibility of treatment with oral anti-platelet agents and screening assays to identify such agents.

The inventor thus reasoned that the zebrafish, in contrast to the mouse and other animals, presents an ideal vertebrate model for studying mammalian hemostasis. In particular, large scale screening is feasible in zebrafish and the hemostatic pathways are similar to those found in man. Indeed, the zebrafish has potential as an excellent model for mammalian hemostasis and thrombosis, since it possesses coagulation factors, thrombocyte receptors and responds to anticoagulant and anti-platelet drugs commonly used in clinical treatment.

C. New Screening Techniques

Animal models for studying thrombosis include those in which blood vessels are ligated. Such methods are time-consuming, invasive and not sufficiently reproducible. In genetic studies, both knockout and transgenic mice may be used. One such example is a transgenic mouse expressing activated protein C (APC)-resistant factor V (U.S. Pat. No. 6,066,778, specifically incorporated herein by reference). Another example is a transgenic mouse with a defective factor XIII gene (U.S. Pat. No. 6,207,877, specifically incorporated herein by reference). However, all such rodent and mouse studies are limited by cost and their labor intensive nature, and often by the specificity of the defect being analyzed.

The zebrafish has been used in screening methods (Driever et al., 1996) for extrinsic pathway defects (Jagadeeswaran et al., 2000a) and certain microassays have been developed to screen for thrombocyte functions in the zebrafish (Gregory & Jagadeeswaran, 2002). However, limitations are present in the zebrafish screening methods possible prior to the present invention, such as discussed in Jagadeeswaran et al. (1999b). One important limitation in the existing screening methods using zebrafish is that the in vitro assays employed are restricted in the spectrum of detectable mutations—primarily to those effecting soluble coagulation factors or platelets.

Therefore, an effective genetic screen for thrombosis that is global and can cover all aspects of Virchow's triad, as necessary to discover thrombotic genetic risk factors, was not available prior to this invention. The present inventor has developed new and improved thrombotic assays using zebrafish, which have demonstrated the ability to detect knockdown phenotypes of hyper- or hypocoagulable states. As disclosed herein, these methods have been applied to screening a population of zebrafish for mutations that affect the time to occlusive thrombus formation, and a mutant locus has been mapped. The invention therefore provides improved assays for use in identifying many of the genes affecting thrombus formation through all of the components of Virchow's triad.

Genetic screens for thrombosis using the zebrafish vascular injury models made possible by the present invention overcome the limitations in the prior art. The new and improved screens thus allow both forward genetic methods, using large-scale mutagenesis, and reverse genetic methods, through targeted knockdown using antisense (morpholino) technology, to be used to identify novel genes affecting thrombosis.

C1. Uniform Wounding via Laser Irradiation

Attempts to measure thrombus formation quantitatively in animal models has long been a challenge to the hemostasis community. Even in zebrafish, the required "uniform wounding" has been difficult to achieve. Since adult zebrafish are large and vary in size, it has been particularly difficult to develop uniform wounding and the art evidences many failed attempts. Since larvae have uniform size, the present inventor first focused on the development of wounding methods for use in larvae.

It was found that agents such as phenylhydrazine (PHZ) and ferric chloride ($FeCl_3$) could be used to cause wounds in zebrafish larvae. However, the limiting factor was not the formation of a visible thrombus, but the formation of a "true thrombus", such as fibrin-rich venous thrombus and thrombocyte-rich arterial thrombus. Artificial hemophilia has also been created in zebrafish larvae using $CuCl_2$, after which blood vessels were punctured with a scalpel blade and bleeding monitored by video camera (Jagadeeswaran and Liu, 1997). In contrast to these and other problematical approaches, the present inventor developed a laser induced injury technique, which successfully achieved the goal of causing a true thrombus, with fibrin and platelets.

Although certain laser wounding techniques have been used in mice, the reproducibility and time required has rendered the practice of such techniques problematical in this animal. Moreover, further screening using mice to discover genes is not possible with the available antisense approaches. Laser wounding has not been previously suggested as applicable for use in zebrafish. However, the inventor surprisingly found that laser-induced injuries could be effectively achieved without the lack of uniformity and other problems observed in the mouse, and that this method was superior to the use of PHZ and $FeCl_3$ in zebrafish.

Accordingly, one of the preferred assay methods of the present invention involves the use of laser ablation in zebrafish larvae to produce a vessel injury that causes a visible vascular occlusion as a result of thrombus formation. This laser irradiation method produces both uniform wounding and a true thrombus. The average time to occlusion (TTO) of laser irradiated vessels in zebrafish larvae was only 17 seconds (±5.0 seconds, n=100), as compared to the 45 minutes typically needed in mouse studies. Moreover, the transparent nature of zebrafish means that observation of the vessels is much simpler than in mice.

Furthermore, the thrombus that is formed via the laser irradiation wounding dissolves after some time, just as occurs in normal thrombus formation in humans. Such lysis of the thrombus was not possible in the phenylhydrazine- or ferric chloride-induced thrombus models. The inventor thus succeeded in developing a reproducible method to create a thrombus, which could be measured by the time to occlude the vessel wall. The time of initiation and propagation of the thrombus can also be measured.

Since there are reliable methods to create mutations in zebrafish, it became possible to create a population of mutants and to measure altered clotting times in each of the mutants. This permits the identification of genes associated with thrombosis, including thrombotic mutations with shortened bleeding times and bleeding-type mutants with prolonged bleeding times. The zebrafish and human versions of such genes can then be isolated by standard methods. In addition, the laser-wounding technology provides a powerful, high throughput method for use in discovering anti-thrombotic compounds in drug development.

Using the time to vascular occlusion as an assay, two screening strategies have already been used successfully to identifying genes involved in thrombosis. Morpholino knockdown studies of zebrafish factor VII showed a prolongation of the time to occlusion of the vessel, whereas knockdown of the recently discovered factor VIIi resulted in a shortening of the time.

A "morpholino" is an antisense oligonucleotide (oligo) with improved properties. Antisense oligos bind and inactivate selected RNA sequences and are useful for studying the function and control of genes and the interaction between gene products. Antisense technology is also an important tool in validating new therapeutic targets, as a first step in drug development. Moreover, antisense oligos are being developed as safe and effective therapeutics for a variety of diseases, including cancer and viral diseases.

Certain antisense oligos may contain backbone modifications, such as methylphosphonates, phosphorodithioates and, particularly, phosphorothioates. Morpholino antisense oligos have advantages over phosphorothioate antisense oligos, such as improved stability, predictable targeting and specificity, thus limiting undesirable non-antisense effects.

Morpholino oligos are assembled from morpholino subunits of adenine, cytosine, guanine and thymine, i.e., the four genetic bases linked to a 6-membered morpholine ring. Typically, 18 to 25 morpholino subunits are joined in the desired order by non-ionic phosphorodiamidate intersubunit linkages to give a Morpholino oligo. Morpholino oligos with 6-membered morpholine backbone moieties joined by non-ionic linkages afford substantially better antisense properties than do RNA, DNA, and their analogs having 5-membered ribose or deoxyribose backbone moieties joined by ionic linkages.

Using the methods of the present invention, genetic screening of a population of zebrafish identified mutants that showed a prolongation of the time to occlusion. Bulk segregant analysis showed linkage of one mutant to a locus, victoria, on linkage group 7. Further characterization of the victoria locus and other mutants should reveal additional novel genes controlling hemostasis and thrombosis. Thus, the laser-induced vascular occlusion assay of the present invention is effective to measure in vivo thrombus formation and is a powerful tool for identifying novel genes involved in thrombosis.

Applying the laser irradiation injury technique in conjunction with the power of saturation mutagenesis screens in zebrafish provides, for the first time, methods suitable to identify most genes affecting thrombus formation through the components of Virchow's triad, ie., blood flow, endothelium, plasma and blood cells (Virchow, 1856). The ability to analyze factors produced by the endothelium and/or platelets is an important advantage over prior art methods. The present vascular injury model in zebrafish is therefore a powerful tool to clarify aspects of the pathways in hemostasis, unresolved by studies in other animal models. Major advantages of the zebrafish model are the clarity of direct visualization of thrombus initiation, propagation, and fibrinolysis (after laser irradiation).

Fluorescent markers for fibrinogen or thrombocytes can also be used in the assays of the invention to detect variations in the rate and level of fibrin formation, as well as the extent of thrombocyte involvement in the developing thrombus. Moreover, studying the lysis of the occlusive thrombus and reversal of the thrombus after laser irradiation can address questions about wound healing, ischemia, and angiogenesis following thrombus resolution. Additionally, unlike the information resulting from genetic analyses of human populations, the ability of anticoagulant drugs to affect TTO indicates that the zebrafish model of the present invention provides a new tool for the screening and discovery of anti-thrombotic drugs.

C2. Uniform Wounding via Sodium Hydroxide

The present invention further provides improved high throughput methods for monitoring hemostasis in the adult zebrafish. Due to the miniature size of zebrafish, prior to this invention it was difficult to establish assays to measure hemostasis and thrombosis in the zebrafish. Some available assays include those using zebrafish plasma to which human fibrinogen has been added. The finding that thrombin generated in the zebrafish plasma can cleave human fibrinogen to form human fibrin led to the development of coagulation assays using human fibrinogen and zebrafish blood obtained by cutting the tail fin with scissors (Jagadeeswaran et al., 2000a). Kinetic assays have also been reported, using blood collected following vessel puncture with a scalpel (Jagadeeswaran et al., 2000a). Functional assays for zebrafish thrombocytes are also available. In certain studies, zebrafish have been treated with aspirin and the blood collected in eppendorf tubes after incision with scissors (Jagadeeswaran et al., 1999a; Jagadeeswaran and Sheehan, 1999).

However, the existing assays for use in adult zebrafish have certain limitations. For example, while the microassays for coagulation and thrombocyte functions could be used independently for screening the respective functions, there was a need for a screening method that could address all the hemostatic functions in adult fish, in an analogous way to the laser wounding assay described above for use in larvae. This is important because hemostatic functions may be more developed in adults. In addition, the available microassays for zebrafish coagulation and thrombocyte functions are more laborious and complex than an ideal assay for use in high throughput screening.

These problems have been resolved by two other aspects of the overall invention, which provide in vivo and in vitro methods to assay coagulation and assess candidate anti-thrombotic functions in adult zebrafish.

As described in connection with the wounding techniques in larvae, the desired "uniform wounding" has proven difficult to achieve in zebrafish. Quick and simple methods to measure the necessary functions also proved elusive and many attempted methods met with failure. Surprisingly, the present inventor discovered that sodium hydroxide caused uniform bleeding in adult zebrafish when added to the water. This led to the development of the sodium hydroxide-induced gill bleeding assay of the invention.

Measuring the prolongation of bleeding using the sodium hydroxide gill bleeding assay is simple, but effective. Candidate substances can be added to the water and their ability to alter bleeding times readily measured. Therefore, exposure of adult zebrafish to sodium hydroxide in conjunction with a panel of test compounds can now be used as an effective means of anti-thrombotic drug discovery, as well as for use in identifying genes involved in hemostasis.

The feasibility of administering oral anticoagulants to zebrafish has been established, including in studies demonstrating the ability of zebrafish to ingest radiographic dye dissolved in the tank water and in dose response studies using the anticoagulant warfarin. Thus, zebrafish ingest sufficient amounts of water to allow dosing with water-soluble oral medications, anticoagulants and test agents in a standard manner.

The warfarin-based and other studies also indicate that drug- or injury-induced hemorrhage can be recognized by morphologic examination of zebrafish, which further facilitates the identification of hemostatic mutants in the present invention. Spontaneous hemorrhage has been observed in the F2 generation of an interbreeding zebrafish population mutagenized with gamma irradiation. Similarly, exposure of normal and warfarinized zebrafish to a number of physical insults, including ultrasound injury, resulted in visible hemorrhage in the tail and fin regions.

C3. Red Cell Lysis Assay

In a third general aspect of the invention, the inventor has developed in vitro assays for use in monitor hemostasis, which can be used in adult zebrafish. This aspect of the invention provides a red cell lysis assay, which is quick, simple and cost-effective and is therefore of significant use in high throughput screening. The inventor discovered that, in presence of a small amount of anticoagulant, zebrafish blood clots along with hemolysis, which could therefore be used to monitor hemostasis. Compounds can be tested for potential effects on plasma components and platelets using this assay.

The red cell lysis assay of the invention has advantages over other assays available for use with zebrafish. One reported assay requires the collection of zebrafish blood, which is diluted with citrate buffer and centrifuged to provide citrated plasma, which is then mixed with other reagents, including calcium chloride and human fibrinogen. Further centrifugation exposes the plasma to calcium chloride, triggering coagulation. A band of clot forms in the middle of the liquid phase in the capillary, and the time from centrifugation to formation of the first visible band can be measured.

In contrast, the simplicity of the present assay is striking. All that is required is for the zebrafish blood to be collected in a heparinized capillary tube, spun in a hematocrit centrifuge and left to stand. After a clot forms, red cell lysis occurs and hemoglobin is released into the plasma, which appears red.

Red cell lysis assays of this simplicity and effectiveness have not been previously suggested for use in humans and other animals, perhaps because the process would take about 24 hours in humans, as opposed to the 30 minutes discovered for zebrafish. However, subsequent to the present invention and in light of this disclosure, such assays can now be adapted for use in humans and other animals, including mice. This can be most readily achieved by reducing the heparin coating in the tube, so that the blood clot and red cell lysis occurs much faster. Accordingly, the present invention also provides red cell lysis assays that can be used in a clinical setting using only a bed-side hematocrit centrifuge.

Using the zebrafish model, approximately 200 leaf extracts from San Antonio Botanical Gardens were screened using this assay, which is essentially a simple observation of red cell lysis, changing the color of plasma to red. The leaf extracts were separately added to the water with the zebrafish. Blood from the zebrafish was then analyzed in the red cell lysis assay. One of the leaf extracts, lamb ears, gave a prolongation of red cell lysis. Further studies using well defined coagulation and thrombocyte assays revealed that the active principle from the leaf is affecting the thrombocyte adhesion.

During the initial exposure to this leaf extract, the zebrafish did not suffer from internal bleeding and they were normal. Importantly, as fish survival and normality is a gold standard in toxicological testing in relation to human exposure and/or consumption, it is evident that the lamb ears compound is not toxic. Therefore, this compound from lamb ears extract is envisioned as an important component of a new drug for use in preventing arterial thrombosis.

D. Identifying Immature Thrombocytes and Platelets

In other embodiments, the inventor has discovered that immature platelets have a role in arterial thrombosis, a major cause of morbidity and mortality (Jagadeeswaran et al., 1999). The inventor first developed methods to selectively label immature platelets in zebrafish, so that they can be identified separately from the total platelet population. Using a zebrafish arterial thrombus generation model, it was then found that immature thrombocytes appear predominantly at the site of injury first, while mature thrombocytes appear at a later stage and have limited participation in arterial thrombosis. In vitro, immature thrombocytes form independent clusters and then aggregate with separate clusters of mature thrombocytes.

Methods were also developed to selectively label immature platelets in mammals, such as human and murine platelets. It was discovered that immature human and mouse thrombocytes also have an important role in arterial thrombosis, whereas mature thrombocytes do not. Through the discovery that immature platelets arrive at sites of injury first, and that such mechanisms are conserved between zebrafish and mammals, the present invention also provides new methods to counteract arterial thrombosis.

Platelets play an important role in arterial thrombosis by adhering to the sub-endothelial surface and subsequently aggregating to form platelet thrombi which can occlude arteries (Gregory & Jagadeeswaran, 2002; Gregory et al., 2002). In mammals, there are two populations of platelets: immature (young or reticulated) platelets and mature (old or non-reticulated) platelets. Immature mammalian platelets have been detected using thiazole orange.

Immature platelets have a shorter half-life (2 days) than the mature platelets (10 days) and are precursors for the mature platelets. An increase in immature platelets has been used as an indication for synthesis of platelets from their megakaryocyte progenitors, known as thrombopoiesis (Rinder et al., 1998b). An increased percentage of immature platelets has been correlated with an increased risk for thrombosis in many conditions, such as in thrombocytosis, in women with pregnancy induced hypertension, and in animals having undergone ovariectomy (Rinder et al., 1994; Takubo et al., 2002; Jayachandran et al., 2003; Saving et al., 2002).

Immature mammalian platelets induced by erythropoietin administration apparently express more adhesive receptors and appear functionally more active than mature platelets in adults and neonates (Rinder et al., 1994; Rinder et al., 1998a; Rinder et al., 1998b; Stohlawetz et al., 2000; Wolf et al., 1997). The role of immature platelets in arterial thrombosis in mammals has remained elusive though, and the existence of immature platelets in zebrafish has not even been demonstrated.

The present invention includes the discovery of immature thrombocytes in zebrafish, which was achieved via the development of methods to specifically label immature zebrafish thrombocytes as opposed to mature zebrafish thrombocytes. The compound DiI was used to selectively label a particular thrombocyte population in zebrafish. Functional and structural studies of the DiI-labeled and unlabelled thrombocytes demonstrated that the DiI-labeled zebrafish thrombocytes correspond to immature human platelets, whereas the unlabelled zebrafish thrombocytes represent the mature human platelets. In zebrafish, human and mouse platelets, it was also discovered that the immature thrombocytes are predominantly involved in arterial thrombosis, whilst the mature thrombocytes have limited participation.

E. Large Scale Saturation Mutagenesis and Cloning

Although the uniform wounding and screening methods of the present invention represent surprising advances, techniques for maintaining and working with zebrafish and cloning genes are well known in the art. The invention can thus be practiced by those of ordinary skill in the art in light of the present disclosure, both as it applies to zebrafish mutagenesis and screening, and to the cloning and analysis of human homologues of zebrafish genes.

Zebrafish can be maintained effectively in 100-gallon, 5-gallon, 2-gallon and 1-liter tanks. Conditions for breeding and raising zebrafish to adults are routine (e.g., U.S. Pat. Nos. 6,380,458, 6,355,415, 6,299,858 and 6,656,449). Procedures for large scale radiation and chemical mutagenesis are also straightforward. For example, to generate mutants by the radiation mutagenesis method, sperm was prepared by removing the testes and mincing the tissue in a buffer at suitable pH with a pestle in an eppendorf tube. Wild-type eggs were squeezed from females, care was exercised not to have any water contact before fertilization, and kept in petri dish before mixing with sperm in water to produce synchronized embryos. After 3 hr, the embryos were irradiated in a petri dish kept in the chamber of a Garnmatory-M irradiator with a cesium-137 source at a dose of approximately 250-300 rads, and the fish raised to adults. Their progeny was tested for the frequency of single locus mutations by mating them with heterozygote albinos. One out of 700 progeny embryos gave the albino phenotype, indicating approximately 0.1% of mutations at the single locus.

Saturation chemical mutagenesis is currently the preferred method for large scale mutagenesis. Saturation chemical mutagenesis of zebrafish with ethyl nitrosourea (ENU) induces point mutations, which is advantageous in that a range of mutant phenotypes can be expected, in contrast to the null phenotypes expected for large deletion mutants more prominent with the radiation method. The possibility of identifing hypofunctioning alleles should counteract, at least in part, inducing mutations that are embryonic lethal.

Males were treated with ENU (2 to 3 mM) for three 1-hr treatments once every other day for total of three days. One to two weeks following the last mutagenesis, the mutagenized males are mated with heterozygous albino females. When at least $\frac{1}{1000}$ progeny are albinos, mutagenesis is successful. Mutagenized males are then bred with normal females and the progeny are raised before testing for frequency of single locus mutations and raising gynogenetic diploids (Streissinger et al., 1981; specifically incorporated herein by reference). A frequency of single locus mutations as high as 1 in 500 can be expected.

In vitro fertilization is performed as follows. Sperm is prepared by grinding testes in an eppendorf tube with a pestle in Hanks buffer and eggs are harvested by gently squeezing the female. The sperm is treated under UV light (to inactivate DNA) and then mixed with the eggs in a petri dish followed by addition of water. The resulting embryos (haploids) are transferred to glass vials and placed in a French Press (Carver hydraulic unit 3912, IN) at 1.4 minutes after fertilization. A pressure of 8000 Psi is applied and slowly released after 6 minutes. This process stops the second meiotic division. Usually 50-80% of offspring are viable. This results in F2 gynogenetic diploids. Three samples can be processed at the same time and six such high pressure treatments can be performed by an individual per day. Thus, 18 in vitro fertilizations and diploidizations can be performed by an individual per day.

The suitability of saturation mutagenesis and screening in zebrafish involves the high frequency of specific single locus mutations generated by chemical mutagenesis. Thus, if there are 10 genes controlling the pathway, one should get mutant numbers ten times larger than the frequency of the single locus. In the present invention, the screening assays concern coagulation. Considering that the number of coagulation and anticoagulation factors is approximately 15, and each of these factors is controlled by at least one regulatory factor, the total number of genes controlling the pathways will be 30. Therefore, screening 1,000 homozygous mutant fish, should obtain 30 mutants. In addition to the above specific mutations, non-specific mutations such as those involved in liver development etc. will also give rise to thrombin activity defects. Thus, the frequency of mutations may be higher than the above value. Isolating at least 60 mutants (twice the number of expected frequency for the coagulation pathway) representing the genes associated with coagulation pathways, about 15 regulatory mutants may be obtained.

The larvae or adult fish from the large scale radiation and/or chemical mutagenesis strategies can then be assayed using any one or more of the new screening techniques of the present invention. Larvae and fish that are defective are kept for analysis and breeding. Although not required for the utility of the invention, additional biochemical and molecular tools for eliminating defects in known genes are available, which allow the focus to be on defects due to mutations in novel genes involved in the initiation of coagulation.

With the current cloning and sequencing technology, once a mutant zebrafish is identified, the mutant locus can be mapped by linkage analysis and the genes in that locus (a megabase area) can be isolated. These techniques have been employed successfully in zebrafish genetics, although not in conjunction with the advantageous screening methods of the present invention. U.S. patent and published application Nos. 6,355,415, 6,380,458, 2003/0028909 and 2002/0187921 are specifically incorporated herein by reference for even further describing and enabling mutagenesis, mapping, gene cloning and sequencing in zebrafish. The cDNAs corresponding to the identified locus are isolated and the human homologue(s) to these cDNAs identified.

In mapping, random amplified polymorphic DNA (RAPD) markers may be utilized to detect linkage. RAPD primers are commercially available in sets from Operon Technologies (Alameda, Calif.), which were utilized to establish the original linkage map of the zebrafish genome (Postlethwait et al., 1994; specifically incorporated herein by reference). Amplified fragments generated by these primers serve as genetic markers to locate the position of the mutation of interest on a RAPD-based linkage map. This identifies the chromosomal location of the novel genes. Evidence of a low frequency of recombination between the mutant locus (phenotype) and a RAPD indicates tight linkage to that locus and permits localization of the mutant locus to 1 of 29 linkage groups currently available.

To obtain a novel gene, coding portions of genes (cDNAs) are isolated from the mutant locus. To achieve this, locus specific genomic clones may be isolated by initially probing BAC or PAC libraries with the linked RAPD marker and then isolating overlapping clones by genome walking. The required libraries are commercially available. Since BAC and PAC libraries have large genomic inserts, clones spanning up to one megabase of DNA can be generated relatively quickly. A significant number of overlapping clones and their mapped positions in the zebrafish genome are available. The mapping information can thus be used to identify and procure overlapping clones from the mutant locus.

Subsequently, genomic clones spanning the mutant locus are used to select coding sequences within that locus by probing cDNA libraries. Isolating and characterizing coagulation factor genes and cDNAs is now straightforward. Once cDNAs are selected, the sequence is determined and compared to known genes. Mutations are identified by comparing the sequences of wild type and mutant cDNAs. Thus, the comprehensive approach of using zebrafish genetics permits the cloning of novel factors in the coagulation cascade.

Identification of human homologues to novel zebrafish genes controlling hemostasis has direct relevance to human disease. The rapid progress in the human genome project and the availability of cDNA sequences permits rapid identification of human homologues by homology searches of Genbank. Human cDNAs can also be selected by PCR methods. Thus, obtaining human homologues is a straightforward undertaking following the screening methods of the invention.

A cDNA sequence for a zebrafish gene is used to isolate or identify the corresponding human member, from Genbank sequences or by isolation using standard cDNA library screening methods. Since the zebrafish genes are identified on the basis of defective hemostatic function, the human homologue will already have a putative function. Identification of genes with a known function is a tremendous advantage in analysis of gene product. Determining how the corresponding human mutation affects the extrinsic pathway is used to establish unequivocally the role of the novel factor in human coagulation and provides direct human relevance. This information can then be used in the treatment of thrombotic disease. For example, target drugs can be prepared to modulate the activity of identified proteases and other novel therapeutic targets.

The following examples are included to demonstrate certain preferred embodiments of the invention. It will be appreciated by those of skill in the art that the techniques disclosed in the examples that follow represent techniques discovered by the inventor to function well in the practice of the invention, and thus can be considered to constitute certain preferred modes for its practice. However, those of skill in the art will, in light of the present disclosure, appreciate that many changes can be made in the specific embodiments that are disclosed and still obtain a like or similar result without departing from the spirit and scope of the invention.

EXAMPLE I

Zebrafish Laser-Wounding Techniques and Screening Asays

The present example describes screening assays in zebrafish for use in identifying mutations in genes that affect thrombus formation, as relevant to the human population. The preferred laser irradiation injury technique, coupled with the power of saturation mutagenesis screens, provides improved methods suitable to identify genes affecting thrombosis in zebrafish and their human homologues and for use in identifying anti-thrombotic compounds.

A. Materials and Methods

1. Vascular Occlusion with $FeCl_3$

Zebrafish were purchased from Ekkwill Waterlife Resources (Florida) and maintained as described (Jagadeeswaran et al., 2000a, specifically incorporated herein by reference). For screening studies, larvae at three to five days postfertilization (dpf) were placed in 500 µL of water and an equal volume of phenylhydrazine (40 mmol/L phenylhydrazine HCl (PHZ), Sigma, MO) or $FeCl_3$ (40 mmol/L) solution was added. Each larva, along with 9 µL of solution, was placed in a 3 mm×1 mm×3 mm well of an acrylic viewing chamber (narrow wells limited the motion of larvae for better viewing). For recording purposes, larvae were also immobilized in agarose, as described below, and 100 µl of either $FeCl_3$ or PHZ were layered on top of the agarose block. Vascular occlusion was recorded using an inverted Olympus microscope equipped with a Javelin MOS solid-state camera (Japan) connected to a VHS recorder.

2. Vascular Occlusion by Laser Irradiation

For laser irradiation treatment, 1 to 5 larvae (3 mm) were placed in 250 µL of water and anesthetized with 10 µl of Tricaine solution (300 μmol/L, Sigma, MO). 250 μL of 1% low-melting agarose solution (at 40° C.) were added to the anesthetized larvae and each larva, along with approximately 100 μL of agarose solution, was positioned inside a viewing well that was formed by placing a plastic ring on a glass microscope slide. Before treatment, water was allowed to soak into the agarose blocks to wash out the anesthetic. Pulsed nitrogen laser light pumped through coumarin 440 dye (445 nm) (MicroPoint Laser system, Photonic Instruments Inc, IL) at seven pulses/second was delivered to larvae for five seconds through a 10× objective on a Nikon Optiphot microscope. The progress of occlusion was recorded using a Nikon CoolPix 995 CCD camera. The time to occlusion (TTO) was taken as the first time point after treatment where blood flow through the injured vessel was completely blocked.

3. Annexin V Binding

Adult zebrafish were placed in a 500 mL solution of phenylhydrazine (5 mmol/L phenylhydrazine HCl, pH 7.2 in 20 mmol/L Tris) or $FeCl_3$ (5 mmol/L) for five minutes and then rinsed with de-ionized water. Two μL of blood were collected, as described (Jagadeeswaran et al., 2000a, specifically incorporated herein by reference), from control or treated zebrafish and blood cells were isolated by centrifugation of the blood sample at 800 g for two minutes, followed by removal of the supernatant. The cell pellet was washed once with 200 μL of PBS, centrifuged and resuspended in 200 μL of binding buffer (ApoAlert; Clontech, Calif.) followed by addition of 5 μL of FITC conjugated Annexin-V (Clontech, Calif.). Samples were incubated for ten minutes in dark at 25° C. and visualized ulsing a 20× UplanApo objective on an Olympus FV500 confocal microscope or processed by flow cytometry (Gregory & Jagadeeswaran, 2002).

4. Kinetic Coagulation Assays

Erythrocytes from control or treated ($FeCl_3$ or PHZ) adult zebrafish were isolated from blood samples by centrifugation at 100 g for two minutes and removal of the supernatant, which contains the white blood cell fraction. White cells were collected from the supernatant by centrifugation at 800 g for two minutes. Cell pellets were washed in 200 μL of PBS, centrifuged and suspended citrate). Kinetic coagulation assays were performed using dilute zebrafish plasma and activation of coagulation by adding RVV-Xa as described (Jagadeeswaran et al., 2000a, specifically incorporated herein by reference) except that 2 μL of cell suspension (erythrocytes or white cells) from control or treated zebrafish were added to the normal zebrafish plasma.

5. Electron Microscopy

Electron microscopic analysis of the occlusion was performed on ultra-thin sections, prepared as described previously (Jagadeeswaran et al., 1999, specifically incorporated herein by reference), of control or treated adult zebrafish. Images were taken with a Philips 208 transmission electron microscope equipped with an AMT digital imaging system.

6. Microinjections

FITC labeled human fibrinogen was generated by reacting 1 mg/mL (500 mM Na-bicarbonate/carbonate buffer, pH 9.5) human fibrinogen (Calbiochem, LaJolla, Calif.) with 20 μg (from a 1 mg/mL DMSO solution) FITC (Sigma, MO) for 2 hours are room temperature followed by dialysis in PBS. Microinjections were performed as described (Gregory & Jagadeeswaran, 2002, specifically incorporated herein by reference). Approximately 4.5 nL of FITC labeled human fibrinogen at 1 mg/mL in PBS or DiI-$C_{18}$ (Molecular Probes, OR) at 20 μM in PBS (diluted from a fresh 10 mM stock solution in dimethyl formamide) were injected into larval circulation. Larvae were embedded in low-melting agarose on a cover glass and assayed by chemical or laser methods as described above. FITC fluorescence was visualized using a 20× UplanApo objective on an Olympus FV500 confocal microscope and DiI-$C_{18}$ fluorescence was observed using a mercury lamp (100W) and a G2A (exciter D535/50) filter cube attached to the Nikon Optiphot microscope. Images were captured as either TIF files using the FV500 imaging system (Olympus) or as JPEG files using a Nikon CoolPix 995 CCD camera on the Nikon microscope.

7. Inhibition of Clotting Factors by Warfarin or Morpholino Knockdowns

Larvae at 2 and 3 dpf were treated with warfarin as described (Hanumanthaiah et al., 2001, specifically incorporated herein by reference) for 24 hours. Larvae were rinsed in water and tested with either chemical or laser methods of vessel injury. Morpholinos (Discovery Genomics Inc.) were designed against 5'-UTR around the translational start site of zebrafish factor VII (Sheehan et al., 2001, specifically incorporated herein by reference or factor VIIi (Hanumanthaiah et al., 2002, specifically incorporated herein by reference). Sequences were as follows:

FVII morpholino (FVIIas), 5'-CAAGCAGCAGACTC ATATTTACTGC-3' (SEQ ID NO:1);

FVIIi morpholino (FVIIias), 5'-GTCACTGACCTCAGC-CTGTTCACAA-3' (SEQ ID NO:2).

For each morpholino a working solution (2 mg/mL) was prepared as previously described (Nasevicius & Ekker, 2000, specifically incorporated herein by reference). Embryos were generated by in vitro fertilization as described (Westerfield, 2000, specifically incorporated herein by reference) and 9 nL of either morpholino solution were injected into the yolk of embryos at the single to four cell stages. Control embryos were microinjected with an equal volume of PBS. Embryos were maintained at 28° C. and screened at 3 dpf. Only, larvae that showed normal blood flow were selected for testing.

8. Linkage Analysis

Clutches of gynogenetic diploid larvae were generated from a natural population of female zebrafish (Ekkwill) by early pressure treatment as described (Jagadeeswaran et al., 2000a; Westerfield, 2000, each specifically incorporated herein by reference) and larvae from each clutch were assayed using $FeCl_3$ or laser irradiation. The females that yielded mutant clutches were selected for mating with male zebrafish of the isogenic WIK strain (Nechiporuk et al., 1999), obtained from Dr. Barry Paw. The progeny (F1) of these matings were grown to sexual maturity and larvae were collected from brother-sister matings.

Larvae were screened for a prolonged TTO with $FeCl_3$ or laser irradiation and genomic DNA was isolated from the individual larva as described (Westerfield, 2000), except DNA was retrieved, after ethanol precipitation, by using the sealed end of a glass capillary. Two pools of genomic DNA from ten normal and ten prolonged TTO larvae were made by mixing and diluting (1:25) aliquots of the genomic DNA stock solutions. Linkage analysis was performed using the method of bulk segregant analysis (Michelmore et al., 19991, specifically incorporated herein by reference). A panel of 214 microsatellite markers (Shimoda et al., 1999) spaced 10 cM apart across the zebrafish genome was used to determine linkage. Markers identified in this screen were tested using individual genomic DNAs in order to confirm linkage.

B. Results

The inventor reasoned that a uniform vascular wounding technique was an important requirement in a genetic screen for thrombosis, which was missing from the techniques reported to be suitable for use with zebrafish. The possibility of generating a reproducible thrombus upon vascular injury was investigated using three technique, phenylhydrazine, $FeCl_3$ and laser irradiation (Jain, 1985; Kurz et al., 1990; Rosen et al., 2001). Treatment of larvae with phenylhydrazine and $FeCl_3$ caused vascular occlusion in the caudal artery (Isogai et al., 2001).

An advantage of the laser irradiation technique of the present invention is that it proved possible to target vascular injury to either veins or arteries. Return of circulation at the site of injury was observed after laser irradiation injury, both $FeCl_3$ and phenylhydrazine injuries were irreversible.

Time to occlusion (TTO) of the injured vessel was found to be reproducible and dependent upon the dose of agent used. A significant decrease in TTO as larvae increased in age from three to five days post-fertilization (dpf) was observed for phenylhydrazine, but not for $FeCl_3$ or laser irradiation injuries. A normal range, taken as one standard deviation below and above the sample mean TTO, was established by assaying larvae at three ($FeCl_3$ and laser irradiation) or four (phenylhydrazine) dpf from a wild type population of zebrafish. TTO was 6±2 (mean±standard deviation) minutes (n=1000) in $FeCl_3$, 10±2.5 minutes (n=500) in phenylhydrazine and 17±5.0 seconds (n=100) in laser irradiation assays.

To demonstrate that the vascular occlusion requires thrombin activity, larvae were incubated with warfarin, a drug known to affect coagulation factor activity (Suttie, 1987). Warfarin did not affect TTO in phenylhydrazine induced vascular occlusion; however, prolongation of TTO in $FeCl_3$ (>10 minutes) and laser irradiation (>1 minute) injuries was noted, suggesting the mechanism of vascular occlusion induced by phenylhydrazine is different from that of $FeCl_3$ or laser irradiation. Further, the ability of warfarin to prolong TTO suggested that coagulation factors participate in vascular occlusion, emphasizing the fact that the occlusive cell mass induced by $FeCl_3$ or laser irradiation injury results from true thrombus forming activity.

Since phenylhydrazine is known to cause externalization of phosphatidylserine (PS) on plasma membrane of erythrocytes (Jain, 1985), blood cells from treated zebrafish were probed with FITC conjugated annexin V, which has a selective affinity for PS. Since these studies required isolation of blood cells, adult zebrafish were used. Studies showed externalization of PS on erythrocytes after phenylhydrazine treatment. Flow cytomnetry revealed that approximately 18% of erythrocytes exhibited externalization of PS after exposure to phenylhydrazine. The exposure of PS on erythrocytes caused a procoagulant state, as noted by the ability of isolated erythrocytes to increase coagulation activity in vitro.

Electron microscopic analysis of the occluded vessel revealed thrombocyte aggregation and fibrin-like fibers in $FeCl_3$ induced thrombus, but not in phenylhydrazine induced occlusive mass, supporting the mechanism of vascular occlusion suggested by the warfarin studies. However, formation of Heinz bodies (Rifkind, 1965) in the erythrocytes and structures similar to these were noted in the plasma of phenylhydrazine treated fish.

To provide evidence for fibrin formation at the site of vascular injury, fluorescently labeled human fibrinogen, a proven substrate for zebrafish thrombin (Jagadeeswaran, 2000a), was microinjected into the circulation of the larvae. Localized fibrin deposition at the site of thrombus formation was observed in both $FeCl_3$ and laser irradiation injuries, but not in phenylhydrazine induced occlusion. Thrombocyte participation in the occlusive mass was investigated by direct in vivo labeling of zebrafish thrombocytes with DiI-$C_{18}$ (Gregory & Jagadeeswaran, 2002). Thrombocytes were found to adhere and to aggregate on the vessel wall at the site of vascular injury induced by either $FeCl_3$ or laser irradiation but not by PHZ injury.

To test the ability of this assay to detect hypercoagulable and hypocoagulable states, studies were performed with antisense morpholinos specifically designed to inhibit zebrafish factor VII (Sheehan, 2001) and factor VIIi, a recently discovered inhibitor for coagulation (Hanumanthaiah et al., 2002). Zebrafish embryos were microinjected with either FVIIas or FVIIias and at 3 dpf embryos that escaped embryonic lethality and had normal blood flow were screened using laser irradiation. Embryos injected with FVIIas morpholino gave a prolonged TTO of 55±9 seconds (n=12) whereas those injected with FVIIias morpholino gave a shortened TTO of 9±3 (n=11) seconds in laser irradiation assays.

To demonstrate the usefulness of this assay in detecting mutations affecting thrombus formation, the inventor screened for homozygous recessive mutations in gynogenetic diploid larvae generated from a natural population of female zebrafish. These larvae were tested using the $FeCl_3$ or laser irradiation method of vascular injury for a significant variation in TTO, which was defined as a TTO-value one standard deviation outside the established normal TTO range.

From a screen of approximately 300 females, thirteen zebrafish were found in which 20 to 40% of their gynogenetic progeny showed a prolonged TTO for $FeCl_3$ as well as laser irradiation induced vascular injury. To identify the mutant locus affecting TTO, one of the females that yielded mutant larvae was crossed with a male from the isogenic WIK strain (Nechiporuk et al., 1999). F1 progeny of this cross were subjected to brother-sister matings. Screening of the progeny (F2) from these matings identified two mating pairs that yielded larvae showing a Mendelian ratio of 1:3 of prolonged TTO to normal TTO.

Genomic DNA was isolated from individual larvae and two DNA pools were created by combining genomic DNA from 10 larvae showing a normal TTO and 10 larvae showing a prolonged TTO. The pools were each subjected to PCR amplification using a panel of microsatellite markers spanning the zebrafish genome to a resolution of 10 cM. Linkage was found to a marker (z10441) approximately 9 cM distal to the prothrombin (Jagadeeswaran et al., 2000b) gene on linkage group 7. Analysis with markers flanking z10441 and LOD score calculations again revealed the locus to be situated approximately 7.5 cM from z10441. Thus, it suggests that the mutant locus, designated herein as victoria, could be coded either by prothrombin or by a novel gene around the prothrombin locus.

C. Discussion

The present example describes three methods by which vascular occlusion and thrombosis were induced, PHZ treatment, $FeCl_3$ treatment and laser irradiation injury. In previous studies in rats, PHZ was reported to generate super oxide-radicals, which cause oxidative damage to the lipid membrane of erythrocytes inducing PS exposure by an unknown mechanism (Jain, 1985). The present results are consistent with the previous observation that exposed PS on erythrocytes increased the rate of thrombin generation (Jain, 1985). However, in those earlier reports, experiments were performed on only erythrocytes. In the present studies, PS externalization and an induced hypercoagulable state was not observed in the white cells of zebrafish blood after PHZ treatment.

The mechanism by which $FeCl_3$ induces vascular damage is unknown, although reports from studies in rats have suggested that this involves fiee radical generation and subsequent damage to endothelial cells and denudation of endothelial cells from the vessel wall (Kurz et al., 1990). As shown in the present example, $FeCl_3$ treatment of the zebrafish larva caused a localization of the thrombus to the end of the caudal artery, which may be due to the close proximity of this vessel to the dermis. Evidence for this is seen in the differential interference contrast images, where $FeCl_3$ is observed to cause injury to all cells through the dermis to the vascular luminal surface and will eventually cause damage throughout the caudal vessels.

In contrast to $FeCl_3$ treatment, laser irradiation injury is limited to the region within the focal plane of the microscope where the laser irradiation is intense enough to cause damage. Thus, when the lumen of the vessel is brought into focus, damage induced by the laser is limited to the vessel wall at the targeted area.

The present example shows that the mechanism by which the vascular occlusion and thrombus are generated is dependent on the injury method. The vascular occlusion caused by PHZ possibly results from changes induced in the morphology or membrane property of red blood cells. Interestingly, erythrocytes from patients with sickle cell disease also demonstrate exposure of PS and a shortened clotting time (Tait & Gibson, 1994). Thus, the PHZ injury model may be applicable to address questions about the contribution of red blood cells in thrombus formation.

The vascular occlusion following $FeCl_3$ and laser irradiation injuries result in a bona fide thrombus formation consisting of fibrin and aggregated thrombocytes. Although both of these methods may be suitable to assay for the thrombus forming potential in zebrafish larvae, the $FeCl_3$ injury model, as presented here, is limited to mechanism of arterial thrombosis. On the other hand, it was possible with the laser irradiation method to generate both arterial and venous thrombi, thus the scope of mutations that are detectable by the laser method are more encompassing.

Prior to validation of the laser irradiation method, as reported in present example, a potential concern was that the occlusion generated may have resulted from thermal coagulation of the blood. No evidence of thermal blood coagulation, such as immediate cellular clumping, was observed in this study. Importantly, the progressive aggregation of thrombocytes on the luminal surface of the targeted vessels is evidence of a true thrombus formation.

A fourth method, which could be adapted for use in zebrafish, is to induce vascular injury with the use of photo-reactive dyes, such as rose bengal, which are believed to cause localized and milder disruption of the vessel wall by the generation of free radicals (Rosen et al., 2001). However, although a variety of experimental injury models are now available to study thrombosis in the zebrafish, the use of the laser irradiation injury method of the present invention has the important advantage of being a unifying wounding technique that produces a true thrombus.

The morpholino study aspects of the present example are the first report of knockdown technology used in a physiological screen in the zebrafish. The results demonstrate that the in vivo time to occlusion assay can detect deficiencies resulting in both hypo- and hypercoagulable states. Furthermore, the FVIIias morpholino studies established that disruption of factor VIIi causes a hypercoagulable state and indicates that factor VIIi functions in vivo as an inhibitory regulator of hemostasis. Thus, the relative ease of both antisense (morpholino) knockdown technology and assaying for thrombus formation shows that the present invention makes possible the high throughput testing of candidate thrombotic genes obtained from genomic information.

EXAMPLE II

Sodium Hydroxide-Induced Gill Bleeding Assays in Zebrafish

The present example describes an in vivo bleeding assay for use in screening methods using adult zebrafish. The simple and cost-effective nature of this method makes it amendable to use in high throughput screening assays.

The adult zebrafish are placed in water containing an effective amount of sodium hydroxide, which was surprisingly discovered to cause uniform bleeding visible at the gills. This method may be used in conjunction with populations of zebrafish prepared using saturation mutagenesis, to provide improved in vivo screening methods suitable to identify genes affecting thrombosis in zebrafish and their human homologues.

The sodium hydroxide gill-bleeding assay may also be used to identify anti-thrombotic compounds, simply by adding the candidate anti-thrombotic compounds to the water and determining their effect on the bleeding visible at the gills. Candidate anti-thrombotic drugs are compounds that reduce the time and/or severity of bleeding in the zebrafish.

EXAMPLE III

Zebrafish Red Cell Lysis Assays and Discovery of Anti-Thrombotic Compound

The present example describes the development of an in vitro red cell lysis assays for use in screening methods using adult zebrafish. The red cell lysis methodology is quick, simple and cost-effective and is ideally suited for use as a high throughput screening assay, e.g., in conjunction with identifying genes involved in thrombosis and/or in the identification of compounds with anti-thrombotic activity.

In this assay, blood from adult zebrafish is collected and placed in a capillary tube in the presence of an effective amount of anticoagulant. A currently preferred anticoagulant is heparin, and heparinized capillary tubes can be used. The capillary tube is spun in a hematocrit centrifuge and left to stand. The time for red cell lysis to occur is measured, which can be determined simply by reference to red color in the plasma portion in the capillary tube. In controls using normal adult zebrafish not exposed to a test compound, red cells lyse rapidly, e.g. within 30 minutes. Therefore, this assay is ideal for use in testing compounds for the ability to shorten or lengthen red cell lysis time.

Using this assay, approximately 200 leaf extracts from San Antonio Botanical Gardens have been screened for anti-thrombotic activity. Leaf extracts were prepared and added separately to the water with the zebrafish. Blood samples from the zebrafish were then analyzed in the red cell lysis assay.

It was determined that two extracts from different leaves altered red cell lysis time in this assay. An extract from lamb ears leaves gave a prolongation of red cell lysis, from about 30 minutes to about an hour. The zebrafish exposed to this leaf extract did not suffer from internal bleeding and were normal, indicating that the lamb ears compound is not toxic. Further studies using well defined coagulation and thrombocyte assays revealed that the active principle from the leaf, a compound of not greater than 10 kD, is affecting thrombocyte adhesion and has anti-platelet activity. This compound is being analyzed using nmr.

EXAMPLE IV

Identification of Immature Platelets in Zebrafish

This example reports that a sub-set of immature platelets can be selectively labeled, and identified separately from the platelet population as a whole, in zebrafish. It is also shown that immature thrombocytes appear predominantly at the site of injury first, while mature thrombocytes appear at a later stage and have limited participation in arterial thrombosis. Further, it is demonstrated that immature thrombocytes form independent clusters and later aggregate with separate clusters of mature thrombocytes, in vitro. Similar results are presented with human and mouse platelets. The present example shows that in vitro platelet clustering and the appearance of immature platelets first at the site of injury are conserved mechanisms, and thus opens new avenues for the prevention of arterial thrombosis.

A. Materials and Methods

1. Labeling of Thrombocytes and Platelets

Thrombocytes were labeled by injecting adult zebrafish using a 27.5G needle with either 20 µL DiI-$C_{18}$ or 2.5 µL of mepacrine (25 µM). For double labeling, both dyes were mixed and injected together. After 10 minutes, blood was collected from zebrafish by a lateral incision as described earlier (Robinson et al., 2000a;b), except that heparin was used an anticoagulant. The DiI labeled thrombocytes were observed by fluorescence with excitation at 549 nm. Mepacrine labeled thrombocytes and doubly labeled thrombocytes were observed by fluorescence with excitation at 400-440 nm. For labeling larval thrombocytes, four day old larvae were used and injections were performed using a microinjection device into the sinus venous.

Mouse platelets were labeled in vivo by injecting both ethidium bromide (100 µL) and mepacrine (100 µL) into the external jugular vein using a 27.5G needle. Human platelets were labeled by addition of 2 µL ethidium bromide (10 µM) and 2 µL mepacrine (25 µM) to 40 µL of whole blood collected in citrate. Blood was collected by a finger pricking with a lancet.

2. Flow Cytometry

The dual labeled thrombocytes were sorted using Becton Dickinson FACS sorter equipped with two channels.

3. Gamma Irradiation of Zebrafish and DiI labeled Thrombocytes 50 adult zebra fish were exposed to 5GY whole body gamma irradiation using a cesium source. They were analyzed for number of total thrombocytes and the DiI labeled thrombocytes at 1 hr after radiation exposure and every 24 hrs thereafter for 7 days. Thrombocytes were labeled by DiI in vivo as described above. 2.52 µL of blood was collected into heparin solution, fixed and diluted 200 times. Total thrombocytes and DiI labeled thrombocytes were counted using a hemocytometer.

4. Measurement of Calcium Waves

DiI labeled and unlabeled thrombocytes were treated with the Calcium dye (Oregon Green BAPTA-1, Molecular Probes, OR) at a working concentration of 1 nM for 2 minutes and then activated by the different agonists, ADP, Ristocetin, Collagen (Sigma). Recordings were done at every 15 second intervals under fluorescent microscope at excitation/emission at 494/523 nm using CoolPix 995 CCD camera. The recordings were then scanned for average green intensity using Sigma Scan Software Pro 5 (SPSS Inc., IL). The intensities were then plotted as a function against time-points. Similar recordings were carried out in presence of the antagonist and non-DiI labeled thrombocytes.

5. Electron Microscopy

To further study the ultra structure of these thrombocytes, they were analyzed by electron microscopy. Enriched population of thrombocytes was fixed immediately using the EM fixative (const). The cells were further processed at the EM facility and scanned for the specific thrombocytes. Images were taken with a Phillips 208 transmission electron microscope equipped with an AMT digital imaging system.

6. In Vitro Platelet Aggregation

20 µL of collagen (2 mg/mL) or ADP (0.2 mmol/L) were added to 20 µL of human blood collected in citrate, where the platelets were labeled in vitro, and incubated at 37° C. for 5 and 15 minutes and the platelet aggregates were visualized under a Nikon Optiphot microscope.

7. In Vivo Arterial Thrombosis

The arterial thrombus was induced in zebrafish larvae by laser and the thrombus formation was recorded. For mouse thrombosis, C57BL mice which were injected with ethidium bromide and mepacrine were used. A small incision was made in abdomen and the mesenteric arterioles were exposed and taped in a Petri dish. The laser was used to induce the thrombosis and the thrombus formation was recorded. From the above recordings the images were captured at different intervals to create the figures of growing thrombus.

B. Results and Discussion

The inventor chose to use zebrafish to study the role of immature platelets in thrombosis, reasoning that zebrafish is an excellent vertebrate genetic model to study mammalian hemostasis and thrombosis, zebrafish thrombocytes have functional and structural similarities to human platelets and arterial thrombi are easy to induce in zebrafish larvae (Rinder et al., 1994; Takubo et al., 2002; Jayachandran et al., 2003). Immature human platelets have been labeled by thiazole orange (Joutsi-Korhonen et al., 2000). Zebrafish thrombocytes have been identified using DiI-$C_{18}$ (DiI) (Gregory & Jagadeeswaran, 2002), but prior to the studies of the present example, it was not known whether separate thrombocyte populations existed in zebrafish, let alone whether any immature platelets that might exist could be selectively labeled.

To resolve these issues, the inventor exposed adult zebrafish to gamma-irradiation to demonstrate the new synthesis of immature thrombocytes similar to that shown in mice. It was found that the total population of thrombocytes increased slightly one day after gamma irradiation. This increase is probably due to the release of thrombocytes from the spleenic reserves (Morrison et al., 2001). Surprisingly, it was found that unlabeled thrombocytes significantly reduced in number and that DiI-labeled thrombocytes increased in number to three times the normal levels four days post-irradiation. This increase in DiI-labeled thrombocytes suggested that these represent newly synthesized immature platelets, whereas the unlabeled thrombocytes correspond to mature platelets. This was unexpected; for example, Gregory & Jagadeeswaran (2002) used DiI to label all thrombocytes, and no selective labeling of thrombocyte sub-sets was identified.

It was also found that arterial thrombus formation was prolonged in zebrafish mutants with reduced numbers of immature thrombocytes as compared to normal zebrafish larvae.

To provide fiter evidence that DiI labeled thrombocytes are immature and unlabeled thrombocytes are mature, their ultrastructure was compared. Separation of these populations was needed for these studies. When mepacrine was injected into zebrafish blood, it was found that mepacrine, which has been used to label human platelets, labeled the entire population of zebrafish thrombocytes. Thus, when using both DiI and mepacrine, the DiI-labeled thrombocytes were orange and the unlabeled thrombocytes were green at 400-440 nm excitation wavelength. Ficoll/hypaque gradients were used to enrich fixed DiI-labeled immature thrombocytes to eliminate the majority of red cells followed by fluorescent activated cell sorting to separate these two populations of thrombocytes. They were then subjected to transmission electron microscopy.

The DiI-labeled thrombocytes showed the presence of granules similar to the size of glycogen granules, rough endoplasmic reticulum and mitochondria. They also showed filopodia similar to the filopodia observed under a fluorescent microscope. The mature thrombocytes were very similar to those reported earlier and had smooth endoplasmic reticulum and other organelles.

The presence of the rough endoplasmic reticulum in immature thrombocytes suggests that protein synthesis is active, and the transport of proteins to the membrane exists. These results are consistent with the fact that the immature human platelets also have rough endoplasmic reticulum and mature platelets have smooth endoplasmic reticulum supporting that DiI-labeled thrombocytes are immature thrombocytes. The presence of glycogen like granules suggests that these thrombocytes are actively utilizing energy in their function.

To further differentiate the immature and mature thrombocytes by functional activity, the calcium release of individual thrombocytes was measured using agonists such as ADP, and collagen. By observing waves of calcium release, it was found that the DiI-labeled thrombocytes release more calcium than the unlabeled thrombocytes. These results suggested that these immature thrombocytes are functionally distinct from the mature forms, similar to differences observed between immature and mature human platelets.

Since immature human platelets have been shown to express more adhesive receptors such as laminin, fibronectin, and thrombospondin, the inventor hypothesized that the DiI-labeled thrombocytes may initiate thrombocyte aggregation. Implicit in this hypothesis is the concept that immature thrombocytes should cluster together because they have more adhesive receptors. To test which of the two populations would aggregate first, aggregation was initiated on dual labeled zebrafish thrombocytes, either with ADP or collagen. It was observed that immature DiI-labeled thrombocyte clusters formed first. After the reaction was complete, it was also found the aggregates had both DiI-labeled thrombocytes and mepacrine labeled thrombocytes.

To further elucidate which population of thrombocytes comes to the wounded site first, laser injury was performed to cause arterial thrombosis on 4-5 day old zebrafish larvae whose thrombocytes were labeled with both DiI and mepacrine by microinjection. Unfortunately, the mepacrine was not easily detectable through the vessels in contrast to the above in vitro assays. Therefore, the entire blood cells were labeled with an excess of thiozole orange or acridine orange along with DiI. It was found that the dual labeled immature thrombocytes were the ones seen at the site of injury first, as noted by the presence of orange thrombocytes in arterial thrombi. Interestingly, immature thrombocytes were found to be predominant and cells labeled green thrombocytes were sparse at the actual site of injury.

Since every aspect of zebrafish hemostasis tested so far has been found to be very similar to that found in mammals, the above studies were extended to mammalian platelets to examine whether similar mechanisms exist in mammals. However, prior to the present example, there was no reported method to differentially label the immature and mature mammalian platelets still retaining the platelet functions. The inventor surprisingly found that ethidium bromide stained only immature platelets. Since ethidium bromide stains immature platelets and mepacrine labels all platelets, a combination of ethidium bromide and mepacrine dyes labeled immature platelets which gave orange fluorescence and distinguished them among mature platelets which had green fluorescence at 400-440 nm excitation.

Using this dual labeling method, the in vitro aggregation of human platelets was investigated. Clustering of human platelets was found, similar to that observed in zebrafish thrombocytes. Testing mouse platelets with the above reagents also yielded similar results.

To test whether immature platelets also participate in arterial thrombus formation in mice, a mixture of ethidium bromide and acridine orange solutions was injected to mouse circulating blood via the external jugular vein and arterial thrombosis was induced by laser injury on mesenteric arterioles. It was observed that the immature platelets were the only participants in the mouse arterial thrombosis, as found in zebrafish.

The results of in vitro clustering in forming both immature and mature thrombocyte clusters, in contrast to in vivo platelet thrombi, which have predominantly immature thrombocytes are intriguing. The inventor reasons that this difference between the in vitro and in vivo results is likely due to high flow rates in the artery where the mature thrombocytes could not aggregate, whereas the more or less stationary in vitro aggregation reaction may have facilitated the participation of mature thrombocytes.

The finding that immature thrombocytes play a major role in arterial thrombosis will permit the identification of surface receptors unique to the immature thrombocytes. In addition to such receptors, the immature thrombocytes may also have distinct signal transduction pathways to establish the specificity of clustering, which can now be determined. The identification of the unique components of the immature thrombocytes will allow for the development of novel anti-immature platelet drugs, e.g. for use in the controlled reduction of immature thrombocyte number and the selective prevention of arterial thrombosis. Furthermore, DNA markers of expressed sequences in immature platelets may be used to predict the risk of arterial thrombus formation.

In summary, the present example established that immature thrombocytes/platelets first appear at the site of arterial injury and are predominant in arterial thrombosis models. It was also demonstrated that the thrombocytes/platelets cluster together forming individual clusters in the in vitro aggregation reactions. After initial clustering, the immature thrombocyte clusters are nonetheless able to recognize the clusters of mature thrombocytes. These studies advance the understanding of arterial thrombosis and platelet aggregation, and provide for the development of unique diagnostic and therapeutic materials.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps and/or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abe, Usuki, Yamaguchi, Kotaki, Iki, Urabe, "Successful treatment with splenic irradiation for idiopathic thrombocytopenic purpura associated with primary immunodeficiency syndrome", Rinsho Ketsueki, 40(11):1181-6, 1999.

Andre, Prasad, Denis, He, Papalia, Hynes, Phillips, Wagner, "CD40L stabilizes arterial thrombi by a beta3 integrin—dependent mechanism", Nat. Med., 8(3):247-52, 2002.

Balasubramanian, Grabowski, Bini, Nemerson, "Platelets, circulating tissue factor, and fibrin colocalize in ex vivo thrombi: real-time fluorescence images of thrombus formation and propagation under defined flow conditions", Blood, 100(8):2787-92, 2002.

Bresch, Beck, Ehlermann, Schlaszus, Urbanek, "A long-term toxicity test comprising reproduction and growth of zebrafish with 4-chloroaniline", Archives of Environmental Contamination and Toxicology, 19(3):419-27, 1990.

Driever, Solnica-Krezel, Schier, Neuhauss, Malicki, Stemple, Stainer, Zwartkruis, Abdelilah, Rangini, Belak, Boggs, "A genetic screen for mutations affecting embryogenesis in zebrafish", Development, 123:37-46, 1996.

Gregory and Jagadeeswaran, "Selective labeling of zebrafish thrombocytes: Quantitation of thrombocyte function and detection during development", Blood Cells Mol. Dis., 28:418-27, 2002.

Gregory, Hanumanthaiah, Jagadeeswaran, "Genetic analysis of hemostasis and thrombosis using vascular occlusion", Blood Cells Mol. Dis. 29:286-295, 2002.

Hanumanthaiah, Thankavel, Day, Gregory, Jagadeeswaran, "Developmental expression of vitamin K-dependent gamma-carboxylase activity in zebrafish embryos: effect of warfarin", Blood Cells Mol. Dis. 27:992-9, 2001.

Hanumanthaiah, Day, Jagadeeswaran, "Comprehensive Analysis of Blood Coagulation Pathways in Teleostei: Evolution of Coagulation Factor Genes and Identification of Zebrafish Factor VIIi", Blood Cells Mol. Dis., 29:57-68, 2002.

Hogan, Weiler, Lord, "Mouse models in coagulation", Thromb. Haemost., 87:563-74, 2002.

Isogai, Horiguchi, Weinstein, "The vascular anatomy of the developing zebrafish: an atlas of embryonic and early larval development", Dev. Biol., 230:278-301, 2001.

Jagadeeswaran and Liu, "A hemophilia model in zebrafish: analysis of hemostasis", Blood Cells Mol. Dis., 23(1):52-57, 1997.

Jagadeeswaran and Sheehan, "Analysis of blood coagulation in the zebrafish", Blood Cells Mol. Dis., 25(15):239-249, 1999.

Jagadeeswaran, Sheehan, Craig, Troyer, "Identification and characterization of zebrafish thrombocytes", Br. J. Haematol., 107:731-8, 1999a.

Jagadeeswaran, Liu, Sheehan, "Analysis of hemostasis in the zebrafish", Chapter 18, In: Methods in Cell Biology, Academic Press, pp 337-357, 1999b.

Jagadeeswaran, Gregory, Johnson, Thankavel, "Haemostatic screening and identification of zebrafish mutants with coagulation pathway defects: An approach to identifying novel haemostatic genes in man", Br. J Haematol., 110: 946-56, 2000a.

Jagadeeswaran, Gregory, Zhou, Zon, Padmanabhan, Hanumanthaiah, "Characterization of zebrafish full-length prothrombin cDNA and linkage group mapping", Blood Cells Mol. Dis., 26:479-89, 2000b.

Jain, "In vivo externalization of phosphatidylserine and phosphatidylethanolamine in the membrane bilayer and hypercoagulability by the lipid peroxidation of erythrocytes in rats", J. Clin. Invest., 76:218-6, 1985.

Jalbert, Rosen, Moons, Chan, Carmeliet, Collen, Castellino, "Inactivation of the gene for anticoagulant protein C causes lethal perinatal consumptive coagulopathy in mice", J. Clin. Invest., 102:1481-8, 1998.

Jayachandran, Owen, Miller, Effects of Ovariectomy on Aggregation, Secretion, and Metalloproteinases in Porcine Platelets, Am. J Physiol. Heart Circ. Physiol., 284 (5):1679-85, 2003.

Joutsi-Korhonen, Sainio, Riikonen, Javela, Teramo, Kekomaki, "Detection of reticulated platelets: estimating the degree of fluorescence of platelets stained with thiazole orange", Eur. J. Haematol., 65(1):66-71, 2000.

Kurz, Main, Sandusky, "Rat model of arterial thrombosis induced by ferric chloride", Thromb. Res. 60:269-80, 1990.

Lange, Gebauer, Markl, Nagel, "Comparison of testing acute toxicity on embryo of Zebrafish, Brachydanio rerio and RTG-2-cytotoxicity as possible alternatives to the acute fish test", Chemosphere, 30(11):2087-2102, 1995.

Michelmore, Paran, Kesseli, "Identification of markers linked to disease-resistance genes by bulked segregant analysis: a rapid method to detect markers in specific genomic regions by using segregating populations", Proc. Natl. Acad. Sci. U.S.A., 88:828-32, 1991.

Morrison, Miyake, Wright Jr, "Histological study of the development of the embryo and early larva of Oreochromis niloticus (Pisces: Cichlidae)", J. Morphol., 247(2): 172-95, 2001.

Nagel, "DarT: the embryo test with the zebrafish Danio rerio—a general model in ecotoxicology and toxicology", ALTEX: Alternativen zu Tierexperimenten, 19(Supp 1):38-48, 2002.

Nasevicius and Ekker, "Effective targeted gene 'knockdown' in zebrafish", Nat. Genet., 26:216-20, 2000.

Nechiporuk, Finney, Keating, Johnson, "Assessment of polymorphism in zebrafish mapping strains", Genome Res., 9:1231-8, 1999.

Neilson, Allard, Fischer, Malmberg, Viktor, "Incorporation of a subacute test with zebra fish into a hierarchical system for evaluating the effect of toxicants in the aquatic environment", *Ecotoxicology and Environmental Safety*, 20(1):82-97, 1990.

Postlethwait, Johnson, Midson, Talbot, Gates, Ballinger, Africa, Andrews, Carl, Eisen, Horne, Kimmel, Hutchison, Johnson, Rodriguez, "A genetic linkage map for the zebrafish", *Science*, 264:699-703, 1994.

Qin, Ototake, Nagoya, Nakanishi, "Graft-versus-host reaction (GVHR) in clonal amago salmon, Oncorhynchus rhodurus", *Vet. Immunol. Immunopathol.*, 89(1-2):83-9, 2002.

Reitsma, "Genetic principles underlying disorders of procoagulant and anticoagulant proteins", In: *Hemostasis and Thrombosis: Basic Principles and Clinical Practice*, Colman, Hirsh, Marder, Salzman, Eds., 4$^{th}$ Ed, Lippincott Williams & Wilkins, Phila., PA., 2001.

Rifkind, "Heinz body anemia: an ultrastructural study. II. Red cell sequestration and destruction", *Blood*, 26:433-48, 1965.

Rinder, Bonan, Anandan, Rinder, Rodrigues, Smith, "Non-invasive measurement of platelet kinetics in normal and hypertensive pregnancies", *Am. J. Obstet. Gynecol.*, 170(1 Pt.1):117-22, 1994.

Rinder, Tracey, Recht, DeCastro, Rinder, McHugh, Smith, "Differences in platelet alpha-granule release between normals and immune thrombocytopenic patients and between immature and old platelets", *Thromb. Haemost.*, 80(3):457-62, 1998a.

Rinder, Schuster, Rinder, Wang, Schweidler, Smith, "Correlation of thrombosis with increased platelet turnover in thrombocytosis", *Blood*, 91(4):1288-94, 1998b.

Robetorye and Rodgers, "Update on selected inherited venous thrombotic disorders", *Am. J. Hematol.* 68:256-68, 2001.

Robinson, MacKie, Machin, Harrison, "Two colour analysis of reticulated platelets", *Clin. Lab. Haematol.*, 22(4):211-3, 2000a.

Robinson, MacHin, Mackie, Harrison, "In vivo biotinylation studies: specificity of labelling of reticulated platelets by thiazole orange and mepacrine", *Br. J. Haematol.*, 108 (4):859-64, 2000b.

Rosen, Raymond, Zollman, Noria, Sandoval-Cooper, Shulman, Merz, Castellino, "Laser-induced noninvasive vascular injury models in mice generate platelet- and coagulation-dependent thrombi", *Am. J. Pathol.*, 158:1613-22, 2001.

Saving, Mankin, Gorman, "Differences in adhesion receptor expression between immature and older platelets and red blood cells of neonates and adults", *J. Pediatr. Hematol. Oncol.*, 24(2):120-4, 2002.

Schafer, "Hypercoagulable states: molecular genetics to clinical practice", *Lancet*, 344:1739-42, 1994.

Sheehan, Templer, Gregory, Hanumanthaiah, Troyer, Phan, Thankavel, Jagadeeswaran, "Demonstration of the extrinsic coagulation pathway in teleostei: identification of zebrafish coagulation factor VII", *Proc. Natl. Acad. Sci. U.S.A.*, 98:8768-73, 2001.

Shimoda, Knapik:, Ziniti, Sim, Yamada, Kaplan, Jackson, de Sauvage, Jacob, Fishman, "Zebrafish genetic map with 2000 microsatellite markers", *Genomics* 58:219-32, 1999.

Stohlawetz, Dzirlo, Hergovich, Lackner, Mensik, Eichler, Kabrna, Geissler, Jilma, "Effects of erytiropoietin on platelet reactivity and thrombopoiesis in humans", *Blood*, 95(9):2983-9, 2000.

Streissinger, Walker, Dower, Knauber, Singer, "Production of clones of homozygous diploid zebra fish (*Brachydanio rerio*)", *Nature*, 291:293-296, 1981.

Suttie, "The biochemical basis of warfarin therapy", *Adv. Exp. Med. Biol.*, 214:3-16, 1987.

Tait and Gibson, "Measurement of membrane phospholipid asymmetry in normal and sickle-cell erythrocytes by means of annexin V binding", *J. Lab. Clin. Med.*, 123: 741-8, 1994.

Takubo, "Reticulated platelet and its clinical significance", *Rinsho Byori*, 50(8):761-7, 2002.

Virchow, In: *Gesammelte Abhandlungen zur wissenschaftlichen Medicin.*, Medinger Sohn & Co., Frankfurt aM, pp. 219-732, 1856.

Westerfield, *The zebrafish book: a guide for the laboratory use of zebrafish* (Danio rerio), 4th Ed., Univ. of Oregon Press, Eugene, 2000.

Williams and Bray, "Genetics of arterial prothrombotic risk states", *Exp. Biol. Med.*, 226:409-19, 2001.

Wolf, Peng, Friese, Gilmore, Burstein, Dale, "Erytbropoietin administration increases production and reactivity of platelets in dogs", *Thromb. Haemost.*, 78(6):1505-9, 1997.

Yin, Huang, Cui, Fiehler, Lasky, Ginsburg, Broze, Jr., "Prothrombotic phenotype of protein Z deficiency", *Proc. Natl. Acad. Sci. U.S.A.*, 97:6734-8, 2000.

Zhu, Raymond, Zheng, et al., "Abnormalities of Development and Hemostasis in gamma-carboxylase deficient mice", *Blood* 92:152a, 1998.

Zoller, Garcia de Frutos, Hillarp, Dahlback, "Thrombophilia as a multigenic disease", *Haematologica*, 84:59-70, 1999.

What is claimed is:

1. A method for creating a uniform vascular wound in a zebrafish larva or zebrafish, comprising:
   (a) subjecting a zebrafish larva to laser irradiation in an amount and for a period of time effective to cause a uniform vascular wound in said zebrafish larva; or
   (b) exposing a zebrafish to water containing sodium hydroxide in an amount and for a period of time effective to cause a uniform vascular wound detectable in the gills of said zebrafish.

2. The method of claim 1, comprising subjecting a zebrafish larva to laser irradiation in an amount and for a period of time effective to cause a uniform vascular wound in said zebrafish larva.

3. The method of claim 2, wherein said zebrafish larva is a zebrafish larva three to five days postfertilization.

4. The method of claim 2, wherein said zebrafish larva is anesthetized.

5. The method of claim 2, wherein said zebrafish larva is immobilized in agarose.

6. The method of claim 2, wherein said laser irradiation is applied to a major blood vessel of said zebrafish larva to cause a uniform injury in said blood vessel.

7. The method of claim 6, wherein said laser irradiation is applied to a major artery or a major vein of said zebrafish larva.

8. The method of claim 1, wherein said zebrafish larva or zebrafish is a mutant or genetically engineered zebrafish larva or zebrafish, or is one of a population of mutant zebrafish larvae or zebrafish produced by large-scale mutagenesis.

* * * * *

UNITED STATES PATENT AND TRADEMARK OFFICE
CERTIFICATE OF CORRECTION

PATENT NO. : 7,357,916 B2
APPLICATION NO. : 10/525571
DATED : April 15, 2008
INVENTOR(S) : Pudur Jagadeeswaran It is certified that error appears in the above-identified patent and that said Letters Patent is hereby corrected as shown below:

Column 3, line 61, replace "zebratish" with --zebrafish--
Column 4, line 24, replace "centrifliging" with --centrifuging--
Column 4, line 36, replace "cells" with --cell--
Column 5, line 48, replace "isianalyzed" with --is analyzed--
Column 6, line 57, replace "Icapillary" with --capillary--
Column 11, line 51, replace "IIb/IIla" with --IIb/IIIa--
Column 13, line 30, replace "vessels in" with --vessels is--
Column 18, line 10, replace "Garnmatory" with --Gammatory--
Column 18, line 24, replace "identifing" with --identifying--
Column 20, line 61, replace "µl" with --µL--
Column 20, line 67, replace "µl" with --µL--
Column 21, line 31, replace "ulsing" with --using--
Column 22, line 21, replace "reference" with --reference)--
Column 25, line 8, replace "fiee" with --free--
Column 27, line 36, replace "used an" with --used as an--
Column 29, line 8, replace "fiter" with --further--

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,357,916 B2 |
| APPLICATION NO. | : 10/525571 |
| DATED | : April 15, 2008 |
| INVENTOR(S) | : Pudur Jagadeeswaran |

It is certified that error appears in the above-identified patent and that said Letters Patent is hereby corrected as shown below:

Col. 1 Line 3-4 insert

--This invention was made with government support under Grant No. HL063792 awarded by the National Institutes of Health. The government has certain rights in the invention.--

Signed and Sealed this

Seventeenth Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,357,916 B2  Page 1 of 1
APPLICATION NO. : 10/525571
DATED : April 15, 2008
INVENTOR(S) : Pudur Jagadeeswaran It is certified that error appears in the above-identified patent and that said Letters Patent is hereby corrected as shown below:

On the title page, item [73] should read:
--Assignee: The Board of Regents of the University of Texas System, Austin, Texas (US)--

Signed and Sealed this

Thirtieth Day of June, 2009

JOHN DOLL
*Acting Director of the United States Patent and Trademark Office*